(12) United States Patent
Kaplan

(10) Patent No.: US 9,636,401 B2
(45) Date of Patent: *May 2, 2017

(54) FLEXIBLE AND/OR ELASTIC BRACHYTHERAPY SEED OR STRAND

(71) Applicant: Microspherix LLC, Boca Raton, FL (US)

(72) Inventor: Edward J. Kaplan, Boca Raton, FL (US)

(73) Assignee: Microspherix LLC, Boca Raton, FL (US)

( * ) Notice: Subject to any disclaimer, the term of this patent is extended or adjusted under 35 U.S.C. 154(b) by 84 days.

This patent is subject to a terminal disclaimer.

(21) Appl. No.: 14/473,159

(22) Filed: Aug. 29, 2014

(65) Prior Publication Data

US 2015/0010470 A1 Jan. 8, 2015

Related U.S. Application Data

(63) Continuation of application No. 13/916,916, filed on Jun. 13, 2013, now Pat. No. 8,821,835, which is a continuation of application No. 12/823,700, filed on Jun. 25, 2010, now Pat. No. 8,470,294, which is a continuation of application No. 10/665,793, filed on Sep. 19, 2003, now Pat. No. 7,776,310, which is a continuation-in-part of application No. 09/861,326, filed on May 18, 2001, now Pat. No. 6,746,661, said application No. 10/665,793 is a continuation-in-part of application No. 09/861,196, filed on May 18, 2001, now Pat. No. 6,514,193.

(60) Provisional application No. 60/412,050, filed on Sep. 19, 2002, provisional application No. 60/249,128, filed on Nov. 16, 2000.

(51) Int. Cl.

| A61K 49/04 | (2006.01) |
| A61K 41/00 | (2006.01) |
| A61K 47/48 | (2006.01) |
| A61K 51/12 | (2006.01) |
| A61N 5/10 | (2006.01) |
| A61K 49/00 | (2006.01) |
| A61B 5/06 | (2006.01) |
| A61L 31/14 | (2006.01) |
| A61L 31/10 | (2006.01) |
| A61L 31/16 | (2006.01) |
| A61L 31/18 | (2006.01) |
| A61B 90/00 | (2016.01) |

(52) U.S. Cl.
CPC .......... *A61K 41/0038* (2013.01); *A61B 5/064* (2013.01); *A61B 90/39* (2016.02); *A61K 47/48992* (2013.01); *A61K 49/00* (2013.01); *A61K 49/0409* (2013.01); *A61K 51/1282* (2013.01); *A61L 31/10* (2013.01); *A61L 31/146* (2013.01); *A61L 31/148* (2013.01); *A61L 31/16* (2013.01); *A61L 31/18* (2013.01); *A61N 5/1007* (2013.01); *A61N 5/1027* (2013.01); *A61B 2090/3966* (2016.02); *A61L 2300/44* (2013.01); *A61N 2005/1023* (2013.01); *A61N 2005/1024* (2013.01)

(58) Field of Classification Search
CPC ........ A61K 49/00; A61K 49/08; A61K 51/00; A61K 51/12
USPC ...... 424/1.11, 1.25, 1.29, 9.4; 623/1.1, 1.34, 623/1.38
See application file for complete search history.

(56) References Cited

U.S. PATENT DOCUMENTS

| 1,578,945 A | 3/1926 | Withers |
| 2,067,589 A | 1/1937 | Antrim |
| 2,153,889 A | 4/1939 | William |
| 2,269,963 A | 1/1942 | Wappler |
| 2,575,138 A | 11/1951 | Slaughter |
| 2,668,162 A | 2/1954 | Lowe |
| 2,703,316 A | 3/1955 | Schneider |
| 2,758,987 A | 8/1956 | Salzberg |
| 3,187,752 A | 6/1965 | Arthur |
| 3,297,033 A | 1/1967 | Emil et al. |
| 3,351,049 A | 11/1967 | Lawrence |
| 3,565,869 A | 2/1971 | DeProspero |
| 3,625,214 A | 12/1971 | Higuchi |
| 3,636,956 A | 1/1972 | Schneider |
| 3,752,630 A | 8/1973 | Schneider |

(Continued)

FOREIGN PATENT DOCUMENTS

| EP | 0030822 | 9/1983 |
| EP | 0292630 | 11/1988 |

(Continued)

OTHER PUBLICATIONS

Ackerman, The pathology of radiation effect of normal and neoplastic tissue, Am. J. Roentgenol. Radium Ther. Nucl. Med., 114(3):447-59 (1972).
Alonso, et al., "Biodegradable microspheres as controlled-release tetanus toxoid delivery systems," Vaccine 12: 299 (1994).
Amersham Health; OncoSeed (Iodine-125 Seeds) http://www.amershamhealty-us.com/oncoseed/; printed Nov. 19, 2003.
Amersham Health; "EchoSeed" ; http://www.amershamhealth-us.com/echoseed/printed Nov. 19, 2003.
Amersham Health; "Rapid Strand Indications" Http;//www.amershamhealth-us.com/products/index.htp?a=i&i=38 printed Nov. 19, 2003.

(Continued)

*Primary Examiner* — Michael G Hartley
*Assistant Examiner* — Jagadishwar Samala
(74) *Attorney, Agent, or Firm* — Pabst Patent Group LLP; Yvonne Y. Shyntum

(57) ABSTRACT

A flexible or elastic brachytherapy strand that includes an imaging marker and/or a therapeutic, diagnostic or prophylactic agent such as a drug in a biocompatible carrier that can be delivered to a subject upon implantation into the subject through the bore of a brachytherapy implantation needle has been developed. Strands can be formed as chains or continuous arrays of seeds up to 50 centimeters or more, with or without spacer material, flaccid, rigid, or flexible.

25 Claims, 6 Drawing Sheets

(56) References Cited

U.S. PATENT DOCUMENTS

| | | |
|---|---|---|
| 3,811,426 A | 5/1974 | Culver et al. |
| 3,839,297 A | 10/1974 | Wassermar |
| 3,867,519 A | 2/1975 | Michaels |
| 3,936,414 A | 2/1976 | Wright et al. |
| 3,993,073 A | 11/1976 | Zaffaroni |
| 4,052,988 A | 10/1977 | Doddi et al. |
| 4,086,914 A | 5/1978 | Moore |
| 4,093,709 A | 6/1978 | Choi |
| 4,141,087 A | 2/1979 | Shalaby et al. |
| 4,167,179 A | 9/1979 | Kirsch |
| 4,247,406 A | 1/1981 | Widder et al. |
| 4,323,055 A | 4/1982 | Kubiatowicz |
| 4,343,715 A | 8/1982 | Bonaventura et al. |
| 4,351,337 A | 9/1982 | Sidman |
| 4,379,138 A | 4/1983 | Pitt et al. |
| 4,391,797 A | 7/1983 | Folkman |
| 4,402,308 A | 9/1983 | Scott |
| 4,412,989 A | 11/1983 | Iwashita et al. |
| 4,416,659 A | 11/1983 | Simpson et al. |
| 4,427,005 A | 1/1984 | Tener |
| 4,441,496 A | 4/1984 | Shalaby et al. |
| 4,452,973 A | 6/1984 | Casey |
| 4,473,670 A | 9/1984 | Kessidis |
| 4,509,506 A | 4/1985 | Windorski |
| 4,510,295 A | 4/1985 | Bezwada |
| 4,569,836 A | 2/1986 | Gordon |
| 4,612,923 A | 9/1986 | Kronenthal |
| 4,616,656 A | 10/1986 | Nicholson |
| 4,621,638 A | 11/1986 | Silvestrini |
| 4,646,741 A | 3/1987 | Smith |
| 4,689,424 A | 8/1987 | Shalaby |
| 4,697,575 A | 10/1987 | Horowitz |
| 4,700,692 A | 10/1987 | Baumgartner |
| 4,702,228 A | 10/1987 | Russell, Jr. |
| 4,706,652 A | 11/1987 | Horowitz |
| 4,741,337 A | 5/1988 | Smith |
| 4,754,745 A | 7/1988 | Horowitz |
| 4,763,642 A | 8/1988 | Horowitz |
| 4,763,671 A | 8/1988 | Goffinet |
| 4,767,628 A | 8/1988 | Hutchinson |
| 4,772,287 A | 9/1988 | Ray |
| 4,784,116 A | 11/1988 | Russell, Jr. |
| 4,789,724 A | 12/1988 | Domb |
| 4,799,495 A | 1/1989 | Hawkins |
| 4,815,449 A | 3/1989 | Horowitz |
| 4,820,844 A | 4/1989 | Kagiya |
| 4,847,505 A | 7/1989 | Suthanthiran |
| 4,885,254 A | 12/1989 | Sung |
| 4,891,165 A | 1/1990 | Suthanthiran |
| 4,916,209 A | 4/1990 | Fung |
| 4,926,860 A | 5/1990 | Stice |
| 4,936,823 A | 6/1990 | Colvin |
| 4,946,435 A | 8/1990 | Suthanthiran |
| 5,000,912 A | 3/1991 | Bendel |
| 5,011,473 A | 4/1991 | Gatturna |
| 5,019,400 A | 5/1991 | Gombotz |
| 5,022,940 A | 6/1991 | Mehoudar |
| 5,030,195 A | 7/1991 | Nardi |
| 5,059,166 A | 10/1991 | Fischell |
| 5,179,189 A | 1/1993 | Domb |
| 5,219,358 A | 6/1993 | Bendel |
| 5,242,373 A | 9/1993 | Scott |
| 5,264,540 A | 11/1993 | Cooper |
| 5,271,961 A | 12/1993 | Mathiowitz |
| 5,284,144 A | 2/1994 | Delannoy |
| 5,296,229 A | 3/1994 | Grandjean |
| 5,322,499 A | 6/1994 | Liprie |
| 5,339,812 A | 8/1994 | Hardy |
| 5,342,283 A | 8/1994 | Good |
| 5,391,139 A | 2/1995 | Edmundson |
| 5,397,816 A | 3/1995 | Reilly |
| 5,403,576 A | 4/1995 | Lin |
| 5,405,309 A | 4/1995 | Carden, Jr. |
| 5,424,288 A | 6/1995 | Order |
| 5,426,143 A | 6/1995 | de Wit |
| 5,429,582 A | 7/1995 | Williams |
| 5,429,583 A | 7/1995 | Paulus |
| 5,429,634 A | 7/1995 | Narciso, Jr. |
| 5,460,592 A | 10/1995 | Langton |
| 5,486,360 A | 1/1996 | Ballagh |
| 5,521,280 A | 5/1996 | Reilly |
| 5,538,726 A | 7/1996 | Order |
| 5,595,979 A | 1/1997 | Snyder |
| 5,620,700 A | 4/1997 | Berggren |
| 5,626,829 A | 5/1997 | Koutrouvelis |
| 5,626,862 A | 5/1997 | Brem |
| 5,640,705 A | 6/1997 | Koruga |
| 5,650,442 A | 7/1997 | Mitchell |
| 5,670,173 A | 9/1997 | Chang |
| 5,670,356 A | 9/1997 | Sherf |
| 5,707,644 A | 1/1998 | Illum |
| 5,713,828 A | 2/1998 | Coniglione |
| 5,746,998 A | 5/1998 | Torchilin |
| 5,755,704 A | 5/1998 | Lunn |
| 5,761,877 A | 6/1998 | Quandt |
| 5,762,950 A | 6/1998 | Yli-Urpo |
| 5,766,618 A | 6/1998 | Laurencin |
| 5,833,593 A | 11/1998 | Liprie |
| 5,860,909 A | 1/1999 | Mick |
| 5,871,437 A | 2/1999 | Alt |
| 5,886,026 A | 3/1999 | Hunter |
| 5,902,310 A * | 5/1999 | Foerster ............... A61K 49/006 606/142 |
| 5,916,998 A | 6/1999 | Ferruti |
| 5,928,130 A | 7/1999 | Schmidt |
| 5,938,583 A | 8/1999 | Grimm |
| 5,997,463 A | 12/1999 | Cutrer |
| 6,007,474 A | 12/1999 | Rydell |
| 6,007,475 A | 12/1999 | Slater |
| 6,010,446 A | 1/2000 | Grimm |
| 6,011,092 A | 1/2000 | Seppala |
| 6,027,446 A | 2/2000 | Pathak |
| 6,030,333 A | 2/2000 | Sioshansi |
| 6,033,404 A | 3/2000 | Melzer |
| 6,039,684 A | 3/2000 | Ildstad |
| 6,040,408 A | 3/2000 | Koole |
| 6,053,858 A | 4/2000 | Bueche |
| 6,066,083 A | 5/2000 | Slater |
| 6,074,337 A | 6/2000 | Tucker |
| 6,077,880 A | 6/2000 | Castillo |
| 6,080,099 A | 6/2000 | Slater |
| 6,086,942 A | 7/2000 | Carden, Jr. |
| 6,099,457 A | 8/2000 | Good |
| 6,099,458 A | 8/2000 | Robertson |
| 6,102,844 A | 8/2000 | Ravins |
| 6,129,670 A | 10/2000 | Burdette |
| 6,132,359 A | 10/2000 | Bolenbaugh |
| 6,132,677 A | 10/2000 | Ohriner |
| 6,132,947 A | 10/2000 | Honan |
| 6,159,143 A | 12/2000 | Lennox |
| 6,163,947 A | 12/2000 | Coniglione |
| 6,200,255 B1 | 3/2001 | Yu |
| 6,200,256 B1 | 3/2001 | Weinberger |
| 6,200,258 B1 | 3/2001 | Slater |
| 6,210,315 B1 | 4/2001 | Andrews |
| 6,213,932 B1 | 4/2001 | Schmidt |
| 6,228,969 B1 | 5/2001 | Lee |
| 6,241,962 B1 | 6/2001 | Nicolini |
| 6,246,898 B1 | 6/2001 | Vesely |
| 6,248,057 B1 | 6/2001 | Mavity |
| 6,251,135 B1 | 6/2001 | Stinson |
| 6,264,599 B1 * | 7/2001 | Slater ................... A61N 5/1027 600/7 |
| 6,264,600 B1 | 7/2001 | Grimm |
| 6,273,851 B1 | 8/2001 | Slater |
| 6,280,704 B1 | 8/2001 | Schutt |
| 6,283,911 B1 | 9/2001 | Keren |
| 6,290,982 B1 | 9/2001 | Seppala |
| 6,311,084 B1 | 10/2001 | Cormack |
| 6,312,374 B1 | 11/2001 | vonHoffmann |
| 6,319,190 B1 | 11/2001 | Schmidt |
| 6,327,490 B1 | 12/2001 | Spetz |
| 6,358,195 B1 | 3/2002 | Green |
| 6,360,116 B1 | 3/2002 | Jackson, Jr. |

(56) References Cited

U.S. PATENT DOCUMENTS

| | | |
|---|---|---|
| 6,368,331 B1 | 4/2002 | Front |
| 6,387,034 B1 | 5/2002 | Lee |
| 6,391,279 B1 | 5/2002 | Singh |
| 6,398,709 B1 | 6/2002 | Ehr |
| 6,402,677 B1 | 6/2002 | Jacobs |
| 6,403,916 B1 | 6/2002 | Spooner |
| 6,416,960 B1 | 7/2002 | Bryan |
| 6,419,621 B1 | 7/2002 | Sioshansi |
| 6,426,145 B1 | 7/2002 | Moroni |
| 6,428,504 B1 | 8/2002 | Riaziat |
| 6,436,026 B1 | 8/2002 | Sioshansi |
| 6,436,682 B1 | 8/2002 | Bryan |
| 6,438,401 B1 | 8/2002 | Cheng |
| 6,440,058 B1 | 8/2002 | Cutrer |
| 6,450,937 B1 | 9/2002 | Mercereau |
| 6,450,938 B1 | 9/2002 | Miller |
| 6,450,939 B1 | 9/2002 | Grimm |
| 6,456,636 B1 | 9/2002 | Koshihara |
| 6,471,631 B1 | 10/2002 | Slater |
| 6,472,675 B2 | 10/2002 | White |
| 6,474,535 B1 | 11/2002 | Shanks |
| 6,482,178 B1 | 11/2002 | Andrews |
| 6,485,705 B1 | 11/2002 | Schneider |
| 6,497,646 B1 | 12/2002 | Candelaria |
| 6,500,109 B2 | 12/2002 | Tokita |
| 6,514,193 B2 | 2/2003 | Kaplan |
| 6,537,192 B1 | 3/2003 | Elliott |
| 6,537,193 B1 | 3/2003 | Lennox |
| 6,539,247 B2 | 3/2003 | Spetz |
| 6,545,384 B1 | 4/2003 | Pelrine |
| 6,548,171 B1 | 4/2003 | Barbera-Guillem |
| 6,549,802 B2 | 4/2003 | Thornton |
| 6,552,179 B1 | 4/2003 | Wood |
| 6,554,760 B2 | 4/2003 | Lamoureux |
| 6,561,967 B2 | 5/2003 | Schmidt |
| 6,569,076 B1 | 5/2003 | Larsen |
| 6,572,525 B1 | 6/2003 | Yoshizumi |
| 6,572,527 B2 | 6/2003 | Steele, Sr. |
| 6,572,608 B1 | 6/2003 | Lee |
| 6,575,888 B2 | 6/2003 | Zamora |
| 6,585,633 B2 | 7/2003 | Vitali |
| 6,586,859 B2 | 7/2003 | Kornbluh |
| 6,595,908 B2 | 7/2003 | Loffler |
| 6,599,231 B1 | 7/2003 | Elliott |
| 6,612,976 B2 | 9/2003 | Rosenthal |
| 6,616,593 B1 | 9/2003 | Elliott |
| 6,616,594 B2 | 9/2003 | Fontayne |
| 6,626,817 B2 | 9/2003 | Luth |
| 6,632,176 B2 | 10/2003 | McIntire |
| 6,638,205 B1 | 10/2003 | Chan |
| 6,638,206 B2 | 10/2003 | Green |
| 6,639,237 B2 | 10/2003 | Pedersen |
| 6,648,811 B2 | 11/2003 | Sierocuk |
| 6,656,106 B2 | 12/2003 | Schmidt |
| 6,656,107 B1 | 12/2003 | Pedersen |
| 6,669,621 B2 | 12/2003 | OHara |
| 6,669,622 B2 | 12/2003 | Reed |
| 6,679,824 B1 | 1/2004 | Reed |
| 6,682,471 B2 | 1/2004 | Steele, Sr. |
| 6,689,043 B1 | 2/2004 | McIntire |
| 6,709,381 B2 | 3/2004 | Munro, III |
| 6,716,156 B2 | 4/2004 | Menuhr |
| 6,719,242 B2 | 4/2004 | Floyd, Jr. |
| 6,723,037 B2 | 4/2004 | Hamazaki |
| 6,726,617 B1 | 4/2004 | Schmidt |
| 6,746,661 B2 | 6/2004 | Kaplan |
| 6,749,554 B1 | 6/2004 | Snow |
| 6,752,753 B1 | 6/2004 | Hoskins |
| 6,755,775 B2 | 6/2004 | Kalas |
| 6,761,680 B2 | 7/2004 | Terwilliger |
| 6,786,858 B2 | 9/2004 | Terwilliger |
| 6,790,170 B2 | 9/2004 | Moody |
| 6,800,055 B2 | 10/2004 | Amols |
| 6,805,898 B1 | 10/2004 | Wu |
| 6,820,318 B2 | 11/2004 | Terwilliger |
| 6,837,844 B1 | 1/2005 | Ellard |
| 6,846,283 B2 | 1/2005 | Green |
| 6,905,455 B2 | 6/2005 | Rapach |
| 6,911,000 B2 | 6/2005 | Mick |
| 6,926,657 B1 | 8/2005 | Reed |
| 6,949,064 B2 | 9/2005 | Lowery |
| 6,969,344 B2 | 11/2005 | Drobnik |
| 6,989,543 B2 | 1/2006 | Drobnik |
| 7,008,367 B2 | 3/2006 | Visscher |
| 7,060,020 B2 | 6/2006 | Terwilliger |
| 7,074,291 B2 | 7/2006 | Terwilliger |
| 7,083,566 B2 | 8/2006 | Tornes |
| 7,094,198 B2 | 8/2006 | Terwilliger |
| 7,118,523 B2 | 10/2006 | Loffler |
| 7,211,039 B2 | 5/2007 | Lamoureux |
| 7,267,643 B2 | 9/2007 | Koster |
| 7,322,928 B2 | 1/2008 | Reed |
| 7,497,818 B2 | 3/2009 | Terwilliger |
| 7,601,113 B2 | 10/2009 | Lebovic |
| 2001/0041835 A1 | 11/2001 | Front |
| 2001/0041838 A1 | 11/2001 | Holupka |
| 2001/0044567 A1* | 11/2001 | Zamora ............... A61K 51/1282 600/3 |
| 2001/0047185 A1 | 11/2001 | Satz |
| 2002/0055666 A1 | 5/2002 | Hunter |
| 2002/0055667 A1 | 5/2002 | Mavity |
| 2002/0058854 A1 | 5/2002 | Reed |
| 2002/0066824 A1 | 6/2002 | Floyd |
| 2002/0077687 A1 | 6/2002 | Ahn |
| 2002/0087078 A1 | 7/2002 | Cox |
| 2002/0114763 A1 | 8/2002 | Glajch |
| 2002/0123660 A1 | 9/2002 | Amols |
| 2002/0156338 A1 | 10/2002 | Menuhr |
| 2003/0003094 A1 | 1/2003 | Hunter |
| 2003/0010508 A1 | 1/2003 | Greiner |
| 2003/0084988 A1 | 5/2003 | Terwilliger |
| 2003/0092958 A1 | 5/2003 | Terwilliger |
| 2003/0129311 A1 | 7/2003 | Huang |
| 2003/0132546 A1 | 7/2003 | Yamauchi |
| 2003/0134959 A1 | 7/2003 | Hancock |
| 2003/0139567 A1 | 7/2003 | Kim |
| 2003/0153804 A1 | 8/2003 | Tornes |
| 2003/0181794 A1 | 9/2003 | Rini |
| 2003/0191355 A1 | 10/2003 | Ferguson |
| 2004/0022517 A1 | 2/2004 | Shiraishi |
| 2004/0024453 A1 | 2/2004 | Castillejos |
| 2004/0109823 A1 | 6/2004 | Kaplan |
| 2004/0158117 A1 | 8/2004 | Drobnik |
| 2004/0158118 A1 | 8/2004 | Drobnik |
| 2005/0049490 A1 | 3/2005 | Mills |
| 2005/0261541 A1 | 11/2005 | Henderson |
| 2006/0015068 A1 | 1/2006 | Amisar |
| 2006/0052654 A1 | 3/2006 | Drobnik |
| 2006/0063960 A1 | 3/2006 | Wissman |
| 2006/0094983 A1 | 5/2006 | Burbank |
| 2006/0121080 A1 | 6/2006 | Lye |
| 2006/0177379 A1 | 8/2006 | Asgari |
| 2006/0224035 A1 | 10/2006 | Russell |
| 2007/0224234 A1 | 9/2007 | Steckel |
| 2007/0238983 A1 | 10/2007 | Suthanthiran |
| 2007/0270781 A1 | 11/2007 | Burgermeister |
| 2008/0208127 A1 | 8/2008 | Kuriyama |

FOREIGN PATENT DOCUMENTS

| | | |
|---|---|---|
| EP | 0466681 | 1/1992 |
| EP | 668088 | 8/1995 |
| EP | 0894503 | 2/1999 |
| EP | 993843 | 4/2000 |
| EP | 1016423 | 7/2000 |
| EP | 1093824 | 4/2001 |
| EP | 1205437 | 5/2002 |
| EP | 1240920 | 9/2002 |
| GB | 2356140 | 5/2001 |
| WO | 9321906 | 11/1993 |
| WO | 9503036 | 2/1995 |
| WO | 9513891 | 5/1995 |
| WO | 9605872 | 2/1996 |
| WO | 9614880 | 5/1996 |

(56) References Cited

FOREIGN PATENT DOCUMENTS

| WO | 9719706 | 6/1997 |
|---|---|---|
| WO | 9801179 | 1/1998 |
| WO | 9953898 | 10/1999 |
| WO | 0005349 | 2/2000 |
| WO | 0005359 | 2/2000 |
| WO | 0064538 | 2/2000 |
| WO | 0032238 | 6/2000 |
| WO | 0033909 | 6/2000 |
| WO | 0041185 | 7/2000 |
| WO | 0043045 | 7/2000 |
| WO | 0051639 | 9/2000 |
| WO | 0057923 | 10/2000 |
| WO | 0061229 | 10/2000 |
| WO | 0136007 | 5/2001 |
| WO | 0149768 | 7/2001 |
| WO | 0187409 | 11/2001 |
| WO | 0230472 | 4/2002 |
| WO | 0234959 | 5/2002 |
| WO | 02068000 | 9/2002 |
| WO | 03066705 | 8/2003 |
| WO | 2008106586 | 9/2008 |

OTHER PUBLICATIONS

Arcos, et al., "Biphasic materials for bone grafting and hyperthermia treatment of cancer," J. Biomed. Mater. Res. 65: 71-78 (2003).
Beck, et al., "A new long-acting injectable microcapsule system for the administration of progesterone" ,Fertil. Steril., 31:545 (1979).
Beer, et al., "Extended release of adenovirus from polymer microspheres: potential use in gene therapy for brain tumors," Adv. Drug Deliv. Rev. 27: 59 (1997).
Bellon, et al., "Use of pelvic CT scanning to evaluate pubic arch interference of transperineal prostate brachytherapy," Int J Radiat Oncol Biol Phys 43(3):579-81 (1999).
Benita et al., "Characterization of drug-loaded poly(d,l-lactide) microspheres", J. Pharm. Sci., 73:1721 (1984).
Benzina, et al., "Studies on a new radiopaque polymeric biomaterial," Biomaterials 15: 1122 (1994).
Blasko, et al., "Brachytherapy for Carcinoma of the Prostate: Techniques, Patient Selection, and Clinical Outcomes," Seminars in Radiation Oncology 12(1): 81-94 (2002).
Bloch, et al., "Prostate postbrachytherapy seed distribution: comparison of high-resolution, contrast-enhanced, T1- and T2-weighted endorectal magnetic resonance imaging versus computed tomography: initial experience", Int. J. Radiat. Oncol. Biol. Phys., 69(1):70-8 (2007).
Bobofchak, et al., "A recombinant polymeric hemoglobin with conformational, functional, and physiological characteristics of an in vivo O2 transporter," Am. J. Physiol. Heart Circ. Physiol. 285: H549-H561 (2003).
Brem, et al., "Biodegradable polymers for controlled delivery of chemotherapy with and without radiation therapy in the monkey brain," J. Neurosurg. 80: 283 (1994).
Brem, et al., "Interstitial chemotherapy with drug polymer implants for the treatment of recurrent gliomas," J. Neurosurg. 74: 441 (1991).
Brem, et al., "Placebo-controlled trail of safety and efficacy of intraoperative controlled delivery by biodegradable polymers of chemotherapy for recurrent gliomas," Lancet 345: 1008 (1995).
Camarata, et al., "Sustained release of nerve growth factor from biodegradable polymer microspheres," Neurosurg. 30: 313 (1992).
Cardinale, et al., "Effect of interstitial and/or systemic delivery of tirapazamine on the radiosensitivity of human glioblastoma multiforme in nude mice," Radiation Oncol. Invest. 6: 63 (1998).
Chattaraj, et al., "Biodegradable microparticles of influenza viral vaccine: comparison of the effects of routes of administration on the in vivo immune response in mice," J. Control. Rel. 58: 223 (1999).
Chen, et al., "Carboplatin-loaded PLGA microspheres for intracerebral implantation: in vivo characterization," Drug Deliv. 4: 301 (1997).
Chen and Blair, "Th—B—224C-01: Permanent prostate brachytherapy using plastic palladium-103 seeds", Med. Phys., 33(6): 2264 (2006). (Abstract).
Chu, et al., "Biodegradable calcium phosphate nanoparticles as a new vehicle for delivery of a potential ocular hypotensive agent," J. Ocular Pharm. Therapeut. 18: 507-514 (2002).
Chuba, et al., "A Case of Strand Migration after Prostate Seed Implant," Poster: ESTRO (2006).
Conforti, et al., "Anti-inflammatory activity of polyphsophazen-based naproxen slow-release systems," J. Pharmacol. 48: 468 (1996).
Cormack, et al., "Optimizing target coverage by dosimetric feedback during prostate brachytherapy," Int. J. Radiation Oncology Biol. Phys. 48(4): 1245-1249 (2000).
Cron, et al., "Changes in the tumor microenvironment during low-dose-rate permanent seed implantation iodine-125 brachytherapy", Int. J. Radiat. Oncol. Biol. Phys., 63(4):1245-51 (2005).
Dash & Cudworth II, "Therapuetica applications of implantable drug delivery systems," JPM 40: 1-12 (1998).
Dawson, et al., "Dose effects of seeds placement deviations from pre-planned positions in ultrasound guided prostate implants," Radiotherapy and Oncology 32: 268-270 (1994).
Doiron, et al., "Tumor radiosensitization by sustained intratumoral release of bromodeoxyuridine," Cancer Res. 59(15): 3677-3681 (1999).
Domb, et al., "Polyanhydrides I: Preparation of high molecular weight polymers," J. Polym. Sci. 25: 3373 (1987).
Duerig, "The use of superelasticity in modern medicine," Materials Research Society 27(2): 101-104 (2002).
During, et al., "Controlled release of dopamine from a polymeric brain implant: in vivo characterization," Ann. Neurol. 25: 351 (1989).
Edleman, et al., "Controlled and modulated release of basic fibroblast growth factor", Biomaterials, 12:619-26 (1991).
Ewend, et al., "Local delivery of chemotherapy and concurrent external beam radiotherapy prolongs survival in metastatic brain tumor models," Research 56: 5217 (1996).
Fichtinger, et al., "System for robotically assisted prostate biopsy and therapy with intraoperative CT guidance," Academic Radiology 9(1): 60-74 (2002).
Fowler, et al., "Evaluation of an implant that delivers leuprolide for one year for the palliative treatment of prostate cancer," Urology 55: 639 (2000).
Frank, et al., "Instruments based on shape-memory alloy properties for minimal access surgery, interventional radiology and flexible endoscopy," Min Invas Ther & Allied Technol 9(2): 89-98 (2000).
Fung, et al., "Pharmacokinetics of interstitial delivery of carmustine, 4-hydroperoxycyclophosphamide, and paclitaxel from a biodegradable polymer implant in the monkey brain," Cancer Res. 58: 672 (1998).
Gacci, et al., "PSA recurrence after brachytherapy for seed misplacement: a double-blind radiologic and pathologic work-up after salvage prostatectomy" , Prostate Cancer Prostatic Dis. 11(1):99-101 (2008). (epub., Oct. 2007, 1-3).
Ganza-Gonzalez, et al., "Chitosan and chondroitin microspheres for oral-administration controlled release of metoclopramide," Eur. J. Pharm. Biopharm. 48: 149-155 (1999).
Garzotto, et al., "Historical perspective on prostate brachytherapy," J. Endourology 14(4): 315-318 (2000).
Geim, et al., "Microfabricated adhesive mimicking gecko foot-hair," Nature Materials 2: 461-463 (2003).
Gobin, et al., "Embolization with radiopaque microbeads of polyacrylonitrile hydrogel: evaluation in swine," Radiology 214: 113 (2000).
Grado, "Techniques to achieve optimal seed placement in salvage and primary brachyterhapy for prostate cancer," Techniques in Urology 6(2): 157-165 (2000).
Grossman, et al., "The intracerebral distribution of BCNU delivered by surgically implanted biodegradable polymers," J. Neurosurg. 76: 640 (1992).

(56) References Cited

OTHER PUBLICATIONS

Hafeli, et al., "Effective targeting of magnetic radioactive 90Y-microspheres to tumor cells by an externally applied magnetic field. Preliminary in vitro and in vivo results," Nuclear Med. Biol. 22: 147 (1995).
Harper, et al., "Enhanced efficacy of a novel controlled release paclitaxel formulation (PACLIMER Delivery System) for local-regional therapy of lung cancer tumor nodules in mice," Clin. Canc. Res. 5: 4242 (1999).
Heintz, et al. "Comparison of I-125 sources used for permanent interstitial implants", Med. Phys., 28(4):671-82 (2001).
Helpap, "Fundamentals on the pathology of prostatic carcinoma after brachytherapy," World J. Urol., 20(4): 207-12 (2002).
Hilgenfeldt, et al., "The acoustics of diagnostic microbubbles: dissipative effects and heat deposition," Ultrasonics 38: 99-104 (2000).
Holm, "The history of interstitial brachytherapy of prostatic cancer," Seminars in Surgical Oncology 13: 431-437 (1997).
Holm, et al., "Transperineal 125iodine seed implantation in prostatic cancer guided by transrectal ultrasonography," J Urol 130(2):283-286 (1983).
Horak, et al., "New radiopaque polyHEMA-based hydrogel particles," J. Biomed. Mat. Res. 34: 183 (1997).
Horiuchi, et al., "Radiotherapy for carcinoma of the tongue with special emphasis on advanced cases," J. Jap. Soc. Cancer Ther. 15(5): 851-857 (1980).
http://investor.mentorcorp.com/news/20010122-32414.cfm, "Mentor Acquires Breakthrough Brachytherapy Technology" (Jan. 25, 2002).
Ikeda, et al. "Polyurethane elastomer with PEO-PTMO-PEO soft segment for sustainedrelease of drugs." Biomaterials 11(8): 553-560 (1990).
Jaiswal, et al., "Long-term multiple color imaging of live cells using quantum dot bioconjugates," Nature Biotechnol. 21: 47-51 (2003).
Jeong, et al., "In vivo biocompatibility and degradation behavior of elastic poly(I-lactide-co-caprolactone) scaffolds", Biomaterials, 25:5939-46 (2004).
Judy, et al., "Effectiveness of controlled release of a cyclophosphamide derivative with polymers against rat gliomas," J. Neurosurg. 82: 481 (1995).
Kakizaki, et al., "Lipidhememicrosphere (LH-M). A new type of totally synthetic oxygen carrier and its oxygen carrying ability," Art. Cells Blood Substit. Immobil. 22: 933-938 (1994).
Kharkevich, et al., "Employment of magnet-susceptible microparticles for the targeting of drugs," J. Pharm. Pharmacol. 41: 286 (1989).
Kong, et al., "Intralesionally implanted cisplatin plus systemic carmustine for the treatment of brain tumors in rats," J. Surg. Oncol. 69: 76 (1998).
Kooy, et al., "A software system for interventional magnetic resonance image-guided guided prostate brachytherapy," Computer Aided Surgery 5: 401-413 (2000).
Kubek, et al., "Prolonged seizure suppression by a single implantable polymeric-TRH microdisk preparation," Brain Res. 809: 189 (1998).
Kunos, et al., "Migration of implanted free radioactive seeds for adenocarcinoma of the prostate using a Mick applicator", Brachytherapy, 3(2):71-7 (2004).
Kunou, et al., "Controlled intraocular delivery of ganciclovir with use of biodegradable scleral implant in rabbits," J. Control. Rel. 37: 143 (1995).
Kuriakose, et al., "Interleukin-12 delivered by biodegradable microspheres promotes the antitumor activity of human peripheral blood lymphocytes in a human head and neck tumor xenograft/scid mouse model," Head & Neck p. 57 (2000).
Lamb, et al., "Analysis of prostate seed loading for permanent implants," J. of Endourology 14(4): 337-341 (2000).
Laurencin, et al., "Bioerodible polyanhydrides for antibiotic drug delivery: in vitro osteomyelitis treatment in a rat model system," J. Orthopaedic Res. 11: 256 (1993).
Lebugle,et al., "Study of implantable calcium phosphate systems for the slow release of methotrexate," Biomaterials 23: 3517-3522 (2002).
Lee et al. Elastic biodegradable poly(glycolide-co-caprolactone) scaffold for tissue engineering, Biomaterials, 66A:29-37 (2003).
Leenstra, et al., "Prostate dimensions and volume in 700 patients undergoing primary surgical or radiotherapeutic management of localized adenocarcinoma: Implications for design of minimally invasive prostate cancer devices", Int. J. Radlat. Oncol. Biol. Phys., 69(3) Supplement: S380-S381 (2007).
Lendlein, et al., "Biodegradable, elastic shape-memory polymers for potential biomedical applications," Science 296: 1673-1676 (2002).
Lester, et al., "Assessment of barium impregnated polyethylene spheres (BIPS®) as a measure of solid-phase gastric emptying in normal dogs—comparison to scintigraphy," Vet. Radiol. Ultrasound 40: 465 (1999).
Li, et al., "Biodistribution of cyclic carbonate of ioxilan: a radiopaque particulate macrophage imaging agent," Acad. Radiol. 3: 500 (1996).
Liang, et al., "Adhesion force measurements on single gecko setae," Solid-State Sensor and Actuator Workshop 33-38 (2000).
Maheshwari et al., "Soluble biodegradable polymer-based cytokine gene delivery for cancer treatment", Mol. Ther. 2:121-30 (2000).
Martinez et al., "Sterilization of 125 I Seeds encased in Vicryl Sutures for Permanent Interstitial Implantation" Intl. J. Radiation Oncology Biol. Phys. vol. 5:411-413, Pergamen Press Ltd, (1979).
Mathiowitz, et al., "Morphology of polyanhydride microsphere delivery systems" , Scanning Microscopy, 4:329 (1990).
Maurer, et al., "Hepatic artery embolization with a novel radiopaque polymer causes extended liver necrosis in pigs due to occlusion of the concomitant portal vein," J. Hepatology 32: 261 (2000).
McLaughlin, et al., "Comparison of day 0 and day 14 dosimetry for permanent prostate implants using stranded seeds", Int. J. Radiat. Oncol. Biol. Phys., 64(1):144-50 (2006).
Medi-Physics brochure entitled I-125 Seeds. No. 6711, Medi-Physics, Inc. Arlington Heights II. 60004, USA; Revised. Oct. 1999, 2 pages.
Medi-Physics brochure entitled I-125 Seeds. No. 7000; Medi-Physics, Inc. Arlington Heights.
Meiller, "Advances May Improve Prostate Cancer Treatment", Boatd of Regents of the University of Wisconsin System, http://www.news,wisc.edu/11899.html, 3 pages (2005).
Menei, et al., "Local and sustained delivery of 5-fluoroacil from biodegradable microspheres for the radiosensitization of glioblastoma," Cancer 86: 325 (1999.
Merrick, et al., "Seed fixity in the prostate/periprostatic region following brachytherapy," Int. J. Radiation Oncol. Biol. Phys. 46: 215-220 (2000).
Mick Needle Former, Catalog # 9910, Mick Radio-Nuclear Instruments, Inc (one page).
Middleton et al., "Synthetic Biodegradable Polymers as Medical Devices", Med. Plas. Biomat. (Mar. 1998).
Minamimura, et al., "Tumor regression by inductive hyperthermia combined with hepatic embolization using dextran magnetite-imcorporated micrsospheres in rates," Int. J. Oncol. 16: 1153-1158 (2000).
Mitsumori, et al., "Development of intra-arterial hyperthermia using a dextran-magnetite complex," Int. J. Hyperthermia 10: 785-793 (1994).
Miyamoto, et al., "Biodegradable scleral implant for intravitreal controlled release of fluconazole," Curr. Eye Res. 16: 930 (1997).
Moorleghem, et al., "Shape memory and superelastic alloys: the new medical materials with growing demand," Bio-Medical Materials & Engineering 8: 55-60 (1998).
Moritera, et al., "Biodegradable microspheres containing adriamycin in the treatment of proliferative vitroretinopathy," Invest. Opthamol. Vis. Sci. 33: 3125 (1992).
Moroz, et al., "Arterial embolization hyperthermia in porcine renal tissue," J. Surg. Res. 105: 209-214 (2002).
Nag, et al., "American Brachytherapy Society (ABS) recommendations for transperineal permanent brachytherapy of prostate cancer," Int J Radiat Oncol Biol Phys 44(4):789-799 (1999).

(56) References Cited

OTHER PUBLICATIONS

Nag, et al., "American Brachytherapy Society Survey of Current Clinical Practice for Permanent Brachytherapy of Prostate Cancer," Brachyther Int 13:243-251 (1997).
Nag, et al., "Intraoperative planning and evaluation of permanent prostate brachytherapy: report of the American Brachytherapy Society," Int. J. Radiation Oncology Biol. Phys. 51(5): 1422-1430 (2001).
Oncura, "RapidStrandRx: The Logical Choice for Improved Dosimetry," Ocura Inc., Plymouth Meeting, PA, Apr. 2005.
Ostertag, et al., "Sequential morphological changes in the dog brain after interstitial iodine-125 irradiation", Neurosurgery, 13(5):523-8 (1983).
Otsuka, et al., "Science and technology of shape-memory alloys: new developments," Materials Research Society 27(2): 91-98 (2002).
Park, et al., "Biodegradable polyanhydride devices of cefazoiin sodium, bupivacaine, and taxol for local drug delivery: preparation and kinetics and mechanism of in vitro release," J. Control. Rel. 52: 179 (1998).
Pathak, et al., "Pubic arch detection in transrectal ultrasound guided prostate cancer therapy," IEEE Transactions on Medical Imaging 17(5): 762-771 (1998).
Perez & Brady, Principles and Practice of Radiation Oncology, 3rd ed, p. 54 (1998).
Perka, et al., "The use of fibrin beads for tissue engineering and subsequential transplantation," Tiss. Eng. 7: 359-361 (2001).
Peschel, et al., "Pubic arch interference in permanent prostate implant patients," J Brachyther Intl 14:241-248 (1998).
Philippe, et al., "Local and sustained delivery of 5-fluoroacil from biodegradable microspheres for the radiosensitization of glioblastoma," Cancer 86: 325 (1999).
Pinkawa, et al., "Evaluation of source displacement and dose-volume changes after permanent prostate brachytherapy with stranded seeds", Radiother. Oncol., 84(2):190-6 (2007).
Pitt et al. "Sustained drug delivery systems II: factors affecting release rates from poly (caprolactone) and related biodegradable polyesters." Journal of pharmaceutical sciences 68(12): 1534-1538 (1979).
Poggi, et al., "Marker and seed migration in prostate localization," Int. J. Radiation Oncol. Biol. Phys. 56: 1248-1251 (2003).
Popowski, et al., "Open magnetic resonance imaging using titanium-zirconium needles: improved accuracy for interstitial brachytherapy implants?" Int. J. Radiation Oncology Biol. Phys. 47(3): 759-765 (2000).
Prestidge, et al., "Post-treatment biopsy results following permanent transrectal ultrasound-guided interstitial brachytherapy in early stage prostate cancer," Int. J. Radiation Oncol. Biol. Phys. 32(Suppl 1): 144 (1995).
Qian, et al., "Fabrication and characterization of controlled release poly(D,L-lactide-co-glycolide) millirods," J. Biomed. Mater. Res. 55: 512 (2001).
Radiomed: Innovative Products for Radiation, "The Visicoil Advantage . . . for Image Guided Radiation Therapy," http://www.radiomed.com/visicoil/, at lease as early as Aug. 2003.
Ramirez, et al., "Biodegradable poly(DL-lactic-co-glycolic acid) microspheres containing tetracaine hydrochloride. In-vitro release profile," J. Microencapsulation 16: 105 (1999).
Reinhard, et al., "Polymeric controlled release of dexamethasone in normal rat brain," J. Control. Rel. 16: 331 (1991).
Ringkjob, "Treatment of intracranial gliomas and metastatic carcinomas by local application of cytostatic agents," Aeta Neurol. Scandinav. 44: 318 (1968).
Roberto, et al., "Structure and dosimetric analysis of biodegradable glasses for prostate cancer treatment," Art. Organs 27: 432-433 (2003).
Saad et al. "Development of degradable polyesterurethanes for medical applications: in vitro and in vivo evaluations." Journal of biomedical materials research 36(1): 65-74 (1997).
Sanchez, et al., "In vivo study of the tissue distribution and immunosuppressive response of cyclosporin A-loaded polyester micro- and nanospheres," Drug Deliv. 2: 21 (1995).
Scheibel, et al., "Conducting nanowires built by controlled self-assembly of amyloid fibers and selective metal deposition," Proc. Natl. Acad. Sci. 100: 4527-4532 (2003).
See, et al., "Brachytherapy and continuous infusion 5-fluorouracil for the treatment of locall advanced, lymph node negative, prostate cancer," Cancer 77(5): 924-927 (1996).
Senderoff, et al., "Fibrin based drug delivery systems," J. Parenter. Sci. Technol. 45: 2-6 (1991).
Seung et al. "Synthesis and characterization of elastic PLGA/PCL/PLGA tri-block copolymers." J Biomater Sci Polymer Edn 13(10): 1163-1173 (2002).
Shikani, et al.,"Polymer chemotherapy for head and neck cancer", Laryngoscope, 110:907-17 (2000).
Sivakumar, et al., "Preparation, characterization and in vitro release of gentamicin from coralline hydroxyapatite-gelatin composite microspheres," Biomaterials 23: 3175-3181 (2002).
Stoeckel, "Nitinol medical devices and implants," Min Invas Ther & Allied Technol 9(2): 81-88 (2000).
Stone, et al., "Prostate brachytherapy in patients with prostate volumes >= 50 cm3: Dosimetic Analysis of Implant Quality," Int. J. Radiation Oncology Biol. Phys. 46(5): 1199-1204 (2000).
Strang, et al., "Real-Time US versus CT Determination of Pubic Arch Interference for Brachytherapy," Radiology 387-393 (2001).
Straw, et al., "Effects of cis-diaminedichloroplatinum II released from D,L-polylactic acid implanted adjacent to cortical allografts in dogs," J. Orthopaedic Res. 12: 871 (1994).
Sundback, et al., "Manufacture of porous polymer nerve conduits by a novel low-pressure injection molding process," Biomaterials 24: 819-830 (2003).
Tamargo, et al., "Growth inhibition of the 9L glioma using polymers to release heparin and cortisone acetate," J. Neurooncol. 9: 131 (1990).
Tamargo, et al., "Interstitial chemotherapy of the 9L gliosarcoma: controlled release polymers for drug delivery in the brain," Cancer Res. 53: 329 (1993).
Tamargo, et al., "Interstitial delivery of dexamethasone in the brain for the reduction of peritumoral edema," J. Neurosurg. 74: 956 (1991).
Tapen, et al., "Reduction of radioactive seed embolization to the lung following prostate brachytherapy," Biomater. 24: 819-830 (2003).
Thanoo, et al., "Tantalum-loaded polyurethane microspheres for particulate embolization: preparation and properties," Biomaterials 12: 525 (1991).
Thanoo & Jayakrishnan, "Radiopaque hydrogel microspheres," J. Microencapsulation 6: 233 (1989).
Tincher, et al., "Effects of pelvic rotation and needle angle on pubic arch interference during transperineal prostate implants," Int. J. Radiation Oncology Biol. Phys. 47(2): 361-363 (2000).
Valtonen, et al., "Interstitial chemotherapy with carmustine-loaded polymers for high-grade gliomas: a randomized double-blind study," Neurosurg. 41: 44 (1997).
Van " t Riet, "Ultrasonically Guided Transperineal Seed Implanation of the Prostate: Modification of the Technique and Qualitative Assessment of Implants", Intl. J. Rad. Onc. Biol. Phys., 24(3):555-558 (1992).
Viroonchatapan, et al., "Preparation and characterization of dextran magnetite-incorporated thermosensitive liposomes: an on-line flow system for quantifying magnetic responsiveness," Pharm. Res. 12: 1176-1183 (1995).
Wada et al. "In vitro evaluation of sustained drug release from biodegradable elastomer." Pharmaceutical Research 8(10):1292-1296 (1991).
Wallner, et al., "An improved method for computerized tomography-planned transperineal 125iodine prostate implants," J Urol 146(1):90-5 (1991).
Wallner, et al., "Use of trus to predict pubic arch interference of prostate brachytherapy," Int. J. Radiation Oncology Biol. Phys 43(3): 583-585 (1999).

(56) References Cited

OTHER PUBLICATIONS

Wallner, et al., Prostate Brachytherapy Made Complicated, pp. 8.24-8.31, SmartMedicine Press: Seattle, 2001.
Walter, et al., "Interstitial taxol delivered from a biodegradable polymer implant against experimental malignant glioma," Cancer Res. 54: 2207 (1994).
Wang, et al., "Transperineal brachytherapy in patients with large prostate glands," Int. J. Cancer 90: 199-205 (2000).
Wang, et al., "A tough biodegradable elastomer," Nature Biotechnol. 20: 602-606 (2002).
Wang, et al., "Intratumoral injection of rhenium-188 microspheres into an animal model of hepatoma," J. Nucl. Med. 39: 1752 (1998).
Watson, "Ultrasound anatomy for prostate brachytherapy," Seminars in Surgical Oncology 13: 391-398 (1997).
Webb, et al., "Biodegradable polyester elastomers in tissue engineering", Expert ZOpin. Biol Ther., 4:801-12 (2004).
Wei, et al., "Carboplatin-loaded PLGA Microspheres for intracerebral implantation: In vivo characterization", Drug Delivery, 4:301 (1997).
Weingart, et al., "Local delivery of dexamethasone in the brain for the reduction of peritumoral edema," Int. J. Cancer 62: 1 (1995).
Williams, et al., "Synthetic, implantable polymers for local delivery of IUDR to experimental human malignant glioma," Int. J. Radiation Oncol. Biol. Phys. 42: 631 (1998).
Wunderlich, et al., "Preparation and biodistribution of rhenium-188 labeled albumin microspheres B 20: a promising new agent for radiotherapy," Appl. Radiation Isotopes 52: 63 (2000).
Yang, et al., "Diagnostic and therapeutic potential of poly(benzyl L-glutamate)," J. Pharm. Sci. 83: 328 (1994).
Yapp, et al., "Cisplatin delivery by biodegradable polymer implant is superior to systemic delivery by osmotic pump or i.p. injection in tumor-bearing mice," Anti-Cancer Drugs 9: 791-796 (1998).
Yapp, et al., "The potentiation of the effect of radiation treatment by intratumoral delivery of cisplatin," Int. J. Radiation Oncol. Biol. Phys. 42: 413 (1998).
Yapp, et al., "Tumor treatment by sustained intratumoral release of cisplatin: effects of drug alone and combined with radiation", Int. J Radiation Oncol. Biol Phys., 39:497-504 (1998).
Yapp et al., "Radiosensitization of a mouse tumor model by sustained intra-tumoral release of etanidazole and tirapazamine using a biodegradable polymer implant device", Radiotherapy Oncol., 53:77-84 (1999).
Yoshida, et al., "In vivo release of cisplatin from a needle-type copolymer formulation implanted in rat kidney," Biomaterials 10: 17 (1989).
Younes, et al., "Synthesis characterization and in vitro degradation of a biodegradable elastomer", Biomaterials, 25:5261-69 (2004).
Yuan, et al., "Implantable polymers for tirapazamine treatments of experimental intracranial malignant glioma," Radiation Oncol. Invest. 7: 218 (1999).
Zelefsky, et al., "Intraoperative conformal optimization for transperineal prostate implantation using magnetic resonance spectroscopic imaging," Cancer J. 6(4) 249-255 (2000).
Zhang, et al., "An all-organic actuator material with a high dielectric constant," Nature 419: 284-287 (2002).vbTab.

\* cited by examiner

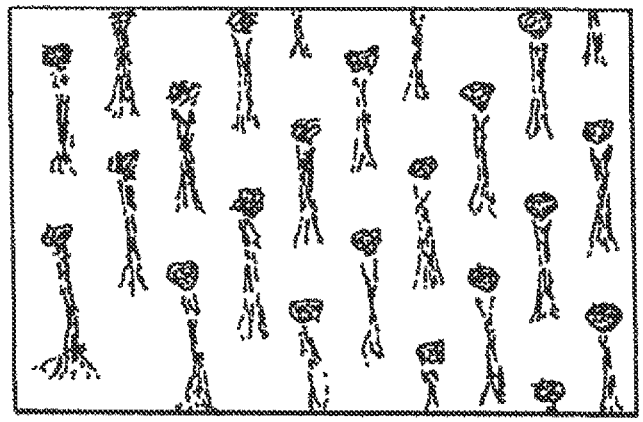
FIG. 6
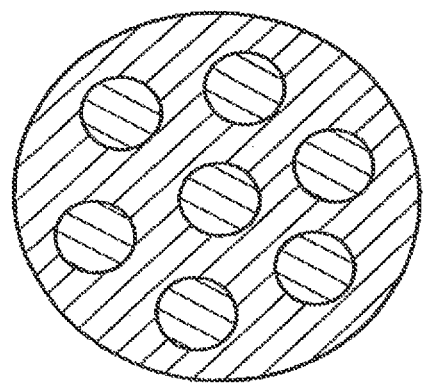
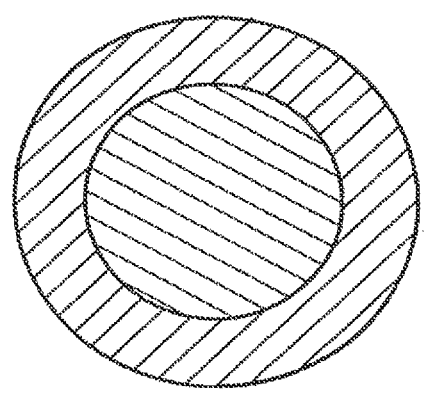
FIG. 7A          FIG. 7B

FLEXIBLE AND/OR ELASTIC BRACHYTHERAPY SEED OR STRAND

The present application is a continuation of U.S. application Ser. No. 13/916,916, filed Jun. 13, 2013, entitled "Flexible and/or Elastic Brachytherapy Seed or Strand", by Edward J. Kaplan, which is a continuation of U.S. application Ser. No. 12/823,700, filed Jun. 25, 2010, now U.S. Pat. No. 8,470,294, issued Jun. 25, 2013, which is a continuation of U.S. application Ser. No. 10/665,793, filed Sep. 19, 2003, now U.S. Pat. No. 7,776,310, issued Aug. 17, 2010, which claims priority to and benefit of U.S. Provisional Application No. 60/412,050, filed Sep. 19, 2002, and is a continuation-in-part of U.S. Ser. No. 09/861,326 filed May 18, 2001, now U.S. Pat. No. 6,746,661, issued Jun. 8, 2004, which claims priority to and benefit of U.S. Provisional Application No. 60/249,128 filed Nov. 16, 2000, and U.S. application Ser. No. 10/665,793, filed Sep. 19, 2003, now U.S. Pat. No. 7,776,310, issued Aug. 17, 2010 is also a continuation-in-part of U.S. Ser. No. 09/861,196 filed May 18, 2001, now U.S. Pat. No. 6,514,193, issued Feb. 4, 2003, which claims priority to and benefit of U.S. provisional application 60/249,128 filed Nov. 16, 2000.

BACKGROUND OF THE INVENTION

This application relates to imagable implantable brachytherapy devices, and methods of use thereof.

Radioactive seed therapy, commonly referred to as brachytherapy, is an established technique for treating various medical conditions, most notably prostate cancer. In a typical application of brachytherapy for treating prostate cancer, about 50-150 small seeds containing a radioisotope that emits a relatively short-acting type of radiation are surgically implanted in the diseased tissue. Because the seeds are localized near the diseased tissue, the radiation they emit is thereby concentrated on the cancerous cells and not on distantly located healthy tissue. In this respect, brachytherapy is advantageous over conventional external beam radiation.

A number of devices have been employed to implant radioactive seeds into tissues. See, e.g., U.S. Pat. No. 2,269,963 to Wappler; U.S. Pat. No. 4,402,308 to Scott; U.S. Pat. No. 5,860,909 to Mick; and U.S. Pat. No. 6,007,474 to Rydell. In a typical protocol for treating prostate cancer, an implantation device having a specialized needle is inserted through the skin between the rectum and scrotum into the prostate to deliver radioactive seeds to the prostate. The needle can be repositioned or a new needle used for other sites in the prostate where seeds are to be implanted. Typically, 20-40 needles are used to deliver between about 50-150 seeds per prostate. A rectal ultrasound probe is used to track the position of the needles. Once the end of a given needle is positioned in a desired location, a seed is forced down the bore of the needle so that it becomes lodged at that location.

As the seeds are implanted in the prostate as desired, the needles are removed from the patient. Over the ensuing several months the radiation emitted from the seeds kills the cancerous cells. Surgical removal of the seeds is usually not necessary because the type of radioisotope generally used decays over the several month period so that very little radiation is emitted from the seeds after this time Currently marketed radioactive seeds take the form of a capsule encapsulating a radioisotope. See, e.g., Symmetra® I-125 (Bebig, GmbH, Germany); IoGold™ I-125 and IoGold™ Pd-103 (North American Scienific, Inc., Chatsworth, Calif.); Best® I-125 and Best® Pd-103 (Best Industries, Springfield, Va.); Brachyseed® I-125 (Draximage, Inc., Canada); Intersource® Pd-103 (International Brachytherapy, Belgium); Oncoseed® I-125 (Nycomed Amersham, UK); STM 1250 I-125 (Sourcetech Medical, Carol Stream, Ill.); Pharmaseed® I-125 (Syncor, Woodland Hills, Calif.); Prostaseed™ I-125 (Urocor, Oklahoma City, Okla.); and I-plant® I-125 (Implant Sciences Corporation, Wakefield, Mass.). The capsule of these seeds is made of a biocompatible substance such as titanium or stainless steel, and is tightly sealed to prevent leaching of the radioisotope. The capsule is sized to fit down the bore of one of the needles used in the implantation device. Since most such needles are about 18 gauge, the capsule typically has a diameter of about 0.8 mm and a length of about 4.5 mm.

The two radioisotopes most commonly used in prostate brachytherapy seeds are iodine (I-125) and palladium (Pd-103). Both emit low energy irradiation and have half-life characteristics ideal for treating tumors. For example, I-125 seeds decay at a rate of 50% every 60 days, so that at typical starting doses their radioactivity is almost exhausted after ten months. Pd-103 seeds decay even more quickly, losing half their energy every 17 days so that they are nearly inert after only 3 months.

Radioactive brachytherapy seeds may also contain other components. For example, to assist in tracking their proper placement using standard X-ray imaging techniques, seeds may contain a radiopaque marker. Markers are typically made of high atomic number (i.e. "high Z") elements or alloys or mixtures containing such elements. Examples of these include platinum, iridium, rhenium, gold, tantalum, lead, bismuth alloys, indium alloys, solder or other alloys with low melting points, tungsten, and silver. Many radiopaque markers are currently being marketed. Examples include platinum/iridium markers (Draximage, Inc. and International Brachytherapy), gold rods (Bebig GmbH), gold/copper alloy markers (North American Scientific), palladium rods (Syncor), tungsten markers (Best Industries), silver rods (Nycomed Amersham), silver spheres (International Isotopes Inc. and Urocor), and silver wire (Implant Sciences Corp.). Other radiopaque markers include polymers impregnated with various substances (see, e.g., U.S. Pat. No. 6,077,880).

A number of different U.S. patents disclose technology relating to brachytherapy. For example, U.S. Pat. No. 3,351,049 to Lawrence discloses the use of a low-energy X-ray-emitting interstitial implant as a brachytherapy source. In addition, U.S. Pat. No. 4,323,055 to Kubiatowicz; U.S. Pat. No. 4,702,228 to Russell; U.S. Pat. No. 4,891,165 to Suthanthiran U.S. Pat. No. 5,405,309 to Carden; U.S. Pat. No. 5,713,828 to Coniglione; U.S. Pat. No. 5,997,463 to Cutrer; U.S. Pat. No. 6,066,083 to Slater; and U.S. Pat. No. 6,074,337 to Tucker disclose technologies relating to brachytherapy devices.

The seeds have also been utilized to treat other types of cancers, such as pancreas, liver, lung and brain. For technical reasons, other organ systems or tissues are not amenable to this type of permanent seed implantation. These include hollow viscera such as the urinary bladder, mobile/muscular viscera such as the base of tongue, and tissues where a cavity or tumor bed has been created as a result of resection, as in the breast. In hollow viscera, loose seeds cannot be reliably spaced out owing to a dearth of tissue and the associated risk of losing the seeds into the lumen or cavity of the organ. Likewise in mobile/muscular and irregularly shaped viscera such as the base of tongue, loose seeds cannot be spaced reliably, and strands of permanent seeds like those described in U.S. Pat. No. 4,754,745 to Horowitz or U.S. Pat. No. 5,322,499 to Liprie are still too inflexible to be used because of the metallic seeds that are embedded within them. Similarly, the wire coils described in U.S. Pat. No. 6,436,026 to Sioshansi, although flexible, are not meant to be implanted permanently and require a means of afterloading and removal.

The situation in breast cancer is similar to that of a hollow organ, whereby loose seeds are difficult to space properly, and may fall into the resection cavity, thus spoiling the dosimetry plan. Despite U.S. Patent application No. 20020087078 by Cox which describes the insertion of a radioactive seed into a breast with cancer, the seed is placed inside the actual breast cancer and is removed along with the tumor at the time of the cancer surgery. Therefore, in this instance, the radioactive seed is not meant to serve a therapeutic purpose. Breast tissue is also similar to the base of tongue or other mobile organs since the breast may be very generous and supple, conforming to forces of gravity or pressure. In fact, for these reasons, metallic seeds are not currently used for permanent therapeutic implantation into a breast.

In each of the above circumstances where use of permanent seeds is not desirable, temporary implants are generally used. This is accomplished via placement of afterloading devices such as the Henschke applicator for cervix cancer, hairpin needles for the base of tongue, and silastic catheters for breast cancer. Once the respective applicators have been placed, radioactive sources are loaded and remain indwelling for a prescribed finite period, usually hours to days. The sources and afterloading devices are then completely removed.

Disadvantages of these temporary systems are that patients often must stay in the hospital for the cadre time that low dose rate sources are indwelling, or between radiotherapy fractions or sessions if high dose rate sources are used. In the case of afterloading catheters, the catheters are sutured in place for several days, causing acute pain, swelling, and possible infection or scarring. In the case of base of tongue implants, patients frequently require temporary tracheostomies to keep their airway open while the hairpin needles remain in place. In one new temporary high dose rate system by Proxima Therapeutics®, surgical placement of a balloon catheter is performed on the breast. The device has a catheter leading from the balloon in the tumor bed to the skin to provide ingress and egress for the temporary brachytherapy source. The balloon is deflated at the conclusion of several days of brachytherapy sessions, and is pulled out of the breast by hand.

It is an object of the present invention to provide biodegradable strands or other structures that are flexible and permanently implantable.

It is another object of the present invention to provide biodegradable strands or other structures that are flexible and implantable.

It is still another object of the present invention to provide non polymeric biodegradable implantable seeds and a means for readily imaging implanted seeds.

It is also an object of the present invention to provide brachytherapy seeds and strands which can be used for ether purposes, for example, drug delivery.

SUMMARY OF THE INVENTION

A brachytherapy strand that is elastic and/or flexible and preferably biodegradable has been developed. A drug or other therapeutically active substance or diagnostic can be included in the strand in addition to, or as an alternative to, a radioisotope. The rate of release in the implantation site can be controlled by controlling the rate of degradation and/or release at the implantation site. In the preferred embodiment, the strands also contain a radioopaque material or other means for external imaging. The flexible material may be polymeric or inorganic material. Strands can be formed as chains or continuous arrays of seeds up to 50 centimeters or more, with or without spacer material, flaccid, rigid, or flexible.

Like conventional radioactive brachytherapy seeds, the strands can be precisely implanted in many different target tissues without the need for invasive surgery. In the preferred embodiment, the strands are implanted into the subject through the bore of a brachytherapy implantation needle or catheter. The therapeutically active substance included within a strand can be delivered in a controlled fashion over a relatively long period of time (e.g., weeks, months, or longer periods). Since concentrations of the therapeutically active substance will be greater at the implantation sue (e.g., the diseased tissue), any potential deleterious effect of the therapeutically active substance on healthy tissue located away from the implantation site will be reduced.

BRIEF DESCRIPTION OF THE DRAWINGS

FIG. 6 is a depiction of microfabricated polyimide hairs used as a coating for the brachytherapy seed or strand to impart adhesive properties.

FIGS. 7A and 7B are transverse cross-section views of a brachytherapy strand with multiple internal conduits (FIG. 7A) or a single conduit (FIG. 7B).

DETAILED DESCRIPTION OF THE INVENTION

Figure 1:
FIG. 1 is a schematic side view of a cylindrically shaped brachytherapy strand.

An elastic and/or flexible, and preferably biodegradable, brachytherapy seed or strand of seeds, has been developed.

As used herein "elastic" refers to a material which has the ability to recover from relatively large deformations, or withstand them, or which can be elongated to multiple times its original length, without breaking. In one preferred embodiment, the brachytherapy strand includes a biocompatible component, a therapeutically active component that includes a non-radioactive drug, and in a more preferred embodiment, a radiopaque marker. The biocompatible component is physically associated with a therapeutically active component and in contact with the marker. In a second embodiment, the brachytherapy strand includes a non-metal biocompatible component, a therapeutically active component comprising a radioisotope, and a radiopaque or other diagnostic marker, the biocompatible component being (a) physically associated with a therapeutically active component and (b) in contact with the diagnostic marker, wherein the brachytherapy strand has a size and shape suitable for passing through the bore of a needle typically having an interior diameter of less than about 2.7 millimeters (10 gauge). In another embodiment, the biocompatible component is biodegradable.

Depending on the particular application, the brachytherapy strands offer other advantages. Among these, for example, compared to conventional systemic administration (e.g., oral or intravenous delivery) of therapeutically active substances, the brachytherapy strands can provide higher and more consistent concentrations of a therapeutically active substance to a target tissue. They can also eliminate the need for repeated injections as well as circumvent delivery problems such as where a target tissue lacks an intact vascular supply (e.g., a target tissue whose blood flow may be compromised) or is otherwise sequestered from the blood supply (e.g., via the blood-brain barrier of the central nervous system). In some embodiments of the strands that do not contain a radioisotope (e.g., those having only the therapeutically active substance and biodegradable component), after the therapeutically active substance is completely released and the biodegradable component is fully decomposed, no foreign device will remain at the implantation site.

I. Brachytherapy Strands.

Brachytherapy strands typically have a size and shape suitable for passing through the bore of a needle having an interior diameter of less than about 2.7 millimeters (10 gauge), less than about 1.4 millimeters (15 gauge), less than about 0.84 millimeters (18 gauge), or less than about 0.56 millimeters (24 gauge). In one version, the strand is shaped into a cylinder having a diameter of between about 0.5 to 3 millimeters and a length of 20, 30, 40 centimeters or more.

A. Materials for Making the Brachytherapy Seeds.

Any appropriate biocompatible material can be used to form the brachytherapy seeds. Preferred materials include polymeric materials which are approved by the Food and Drug Administration for plantation.

In the preferred embodiment, the seeds are formed of a biodegradable material. Examples of suitable materials include synthetic polymers such as polyhydroxyacids (polylactic acid, polyglycolic-lactic acid), polyanhydrides (poly (bis(p-carboxyphenoxy) propane anhydride, poly(bis(p-carboxy) methane anhydride), copolymer of poly-carboxyphenoxypropane and sebacic acid); polyorthoesters; polyhydroxyalkanoates (polyhydroxybutyric acid); and poly (isobtaylcyanoacrylate). Other examples include open cell polylactic acid; co-polymers of a fatty acid dimer and sebacic acid; poly(carboxyphenoxy) hexane; poly-1,4-phenylene dipropionic acid; polyisoplithalic acid; polydodecanedioic acid; poly(glycol-sebacate) (PGS); or other polymers described below. See, e.g., Biomaterials Engineering and Devices: Human Applications: Fundamentals and Vascular and Carrier Applications, Donald L. Wise et al. (eds), Humana Press, 2000; *Biomaterials Science: An Introduction to Materials in Medicine*, Buddy D. Ratner et al. (eds.), Academic Press, 1997; and *Biomaterials and Bioengineering Handbook*, Donald L. Wise, Marcel Dekker, 2000.

These polymers can be obtained from sources such as Sigma Chemical Co., St, Louis, Mo.; Polysciences, Warrenton, Pa.; Aldrich, Milwaukee, Wis.; Fluke, Ronkonkoma, N.Y.; and BioRad, Richmond, Calif., or can be synthesized from monomers obtained from these or other suppliers using standard techniques.

In addition to synthetic polymers, natural polymers may also be used. In the preferred embodiment, the natural polymers are biodegyadable. For example, tissue such as connective tissue from the walls of blood vessels or extracellular matrix may be used as a biodegradable carrier for delivery of radiation or another therapeutic substance. See, for example, U.S. Pat. No. 5,429,634 to Narcisco. Tissue may be autologous, heterologous, engineered, or otherwise modified so long as it is biocompatible with the target tissue. A patient may donate his own tissue to serve as a carrier for the therapeutic substance and/or radionuclide. Other tissues or natural polymers may serve as the degradable carrier matrices. For example, polysaccharides such as starch and dextran, proteins such as collagen, fibrin (Perka, et al., Tissue Eng. 7:359-361 (2001) and Senderoff, et al., J. Parenteral Sci. 45:2-6 (1991)), and albumin (see, for example, U.S. Pat. No. 5,707,644 to Ilum), elastin-like peptides, lipids, and combinations thereof. These materials can be derived from any of the sources known to those skilled in the art, including the patient's own tissues or blood.

Seeds or strands can also be made from synthetic or natural biocompatible non-polymeric and/or inorganic materials, which are preferably biodegradable. See for example, WO 99/53898 describing bioabsorbable porous silicon seeds and WO 00/50349 describing biodegradable ceramic fibers from silica sols. Other examples of non-polymeric and/or organic materials include: U.S. Pat. No. 5,640,705 to Koruga describing radiation-containing fullerene molecules; WO 02/34959A2 by Yeda Research and Development Co, Ltd. describing inorganic fullerene-like nanoparticles or structures; EP 1205437A1 to Osawa describing nano-size particulate graphite and multi-layer fullerene; U.S. Pat. No. 5,766,618 to Laurencin describing a polymeric-hydroxyapatite bone composite; GB 235140A to Asako Matsushima describing a ceramic composite such as hydroxyapatite for sustained release; and U.S. Pat. No. 5,762,950 to Antti Yli-Urpo disclosing a calcium phosphate, e.g. hydroxyapatite, bioactive ceramic for timed release.

In the case of radioactive seeds, it can be left to the clinician to select from any number of biodegradable carder matrices which contain the radionuclide, so king as the degradation characteristics of the carrier substance are consistent with the desired absorption profile. This is because the carrier matrix itself will be sequestered from the surrounding target tissue along with the radionuclide until the radionuclide has decayed to an insignificant activity. At that time or afterwards, the biodegradable layer overlying the radioactive matrix will be eroded away, thus beginning is similar process for the now non-radioactive or nearly spent radioactive carder.

Strands may also be made of non-biodegradable materials, especially the radioopaque strand materials currently used to form beads for treatment of prostate cancer, although this is not as preferred as the biodegradable materials. As described above, the capsule (and as described herein, the strand) of these seeds is made of a biocompatible substance such as titanium or stainless steel, which is tightly sealed to prevent leaching of the radioisotope.

B. Radioactive Tracers

Optionally, brachytherapy seed or strand can be imparted with a means of tracing the radioactive contents should those contents be released inadvertently. Unforeseen problems associated with leakage of radioactive material, whether it be into the surrounding tissues in a patient, in a pathology lab, in a nuclear medicine lab, or in the operating room have been recently discovered as they relate to polymer seeds. The seed/strand should contain a means of tracing their contents should those contents be released inadvertently. This mechanism can rely on inclusion of fluorescent, luminescent, colored, pigmented or other approaches for tagging, detecting, or otherwise identifying the seed/strand contents either visually or with instrument assistance.

Fluorescence can be imparted using the appropriate polymer or other biodegradable substance, such as described by Sung in U.S. Pat. No. 4,885,254, Bryan in U.S. Pat. No. 6,416,960 B1, Barbera-Guillem in U.S. Pat. No. 6,548,171 B1, or Greiner in U.S. Patent Application No. 2003/0010508A1.

Luminescence can be imparted using the appropriate polymer or other biodegradable substance, such as described by Towns in WO01/49768 A2, Sakakibara in EP 1 311 138 A1, Bryan in U.S. Pat. No. 6,436,682B1, Hancock in U.S. Patent Application No. 2003/0134959A1, or Wood in U.S. Pat. No. 6,552,179B1. Bioluminescence materials are described in U.S. Pat. No. 5,670,356. In addition, chemiluminescent and electro luminescent substances might be utilized, as we as other types of luminescent substances as would be known to one skilled in the art.

Quantum dots may also be loaded into the seeds and utilized to locate spilled substances from ruptured seeds/strands, like those described in U.S. Patent Application No. 2003/0129311A1 or Dobson in WO 95/13891 (see also Jaiswal et al., *Nature Biotechnology* 2003; 21:47-51, and Quantum Dot Corporation's Qdot™ biotin conjugate).

Dyed biodegradable polymeric material may be used, as described by Burkhard in EP 1 093 824 A2. Other dyes can be used as indicated. Ultraviolet light can be utilized to detect a therapeutic agent like radioactive substances or drugs using a format described by Koshihara in U.S. Pat. No. 6,456,636 B1, or by Nakashima in WO 00/53659. Infrared dyes may be used, as described by Paulus in U.S. Pat. No. 5,426,143.

Those skilled in the art will be familiar with labeling, doping, or tagging the contents of the seeds/strands with agents that can be identified without modification, or pro-agents that can be identified by the addition of an activating substance or other means, such as labeled antibodies and the like.

C. Therapeutic and Diagnostic Agents

Polymers can be used to form, or to coat, drug delivery devices such as strands or strands containing any of a wide range of therapeutic and diagnostic agents. Any of a wide range of therapeutic, diagnostic and prophylactic materials can be incorporated into the strands, including organic compounds, inorganic compounds, proteins, polysaccharides, and nucleic acids, such as DNA, using standard techniques.

The non-radioactive drug can take the form of stimulating and growth factors; gene vectors; viral vectors; anti-angiogenesis agents; cytostatic, cytotoxic, and cytocidal agents; transforming agents; apoptosis-inducing agents; radiosensitizers; radioprotectants; hormones; enzymes; antibiotics; antiviral agents; mitogens; cytokines; anti-inflammatory agents; immunotoxins; antibodies; or antigens. For example, the non-radioactive therapeutic can be an anti-neoplastic agent such as paclitaxel, 5-fluorouracil, or cisplatin. It can also be a radiosensitizing agent such as 5-fluorouracil, etanidazole, tirapazamine, bromodeoxyuridine (BUdR) and iododeoxyuridine (IUdR).

Many different therapeutically active substances have been associated with biocompatible materials for use in drug delivery systems apart from brachytherapy strands. These include, for example, adriamycin (Moritera et al., *Invest. Ophthal. Vis. Sci.* 33:3125-30, 1992); bupivicaine (Park et al., *J. Controlled Release* 52:179-189, 1998); camptothecin (Weingart et al., *Int. J. Cancer* 62:1-5, 1995); carboplatin (Chen et al., *Drug Delivery* 4:301-11, 1997); carmustine (Brem et al., *J. Neurosurg* 74:441-6, 1991; and U.S. Pat. Nos. 4,789,724 and 5,179,189); cefazolin (Park et al., *J. Controlled Rel.* 52:179-189, 1998); cisplatin (Yapp et al., *IJROBP* 39:497-504, 1997); cortisone (Tamargo et al., *J. Neurooncol.* 9:131-8, 1990); cyclosporine (Sanchez et al., *Drug Delivery* 2:21-8, 1995); daunorubicin (Dash et al., *J. Pharmacol. Tox. Meth.* 40:1-12, 1999); dexamethasone (Reinhard et al., *J Contr. Rel.* 16:331-340, 1991); dopamine (During et al., *Ann. Neurol.* 25:351-6, 1989); etanidazole (Yapp et al., *Radiotherapy Oncol.* 53:77-84, 1999); 5-fluorouracil (Menei et al., *Cancer* 86:325-30, 1999); fluconazole (Miyamoto et al., *Curr. Eye Res.* 16:930-5, 1997); 4-hydroxycyclophosphamide (Judy et al., *J. Neurosurg,* 82:481-6, 1995); ganciclovir (Kunou et al., *J. Controlled Rel.* 37:143-150, 1995); gentamicin (Laurentin et al., *J. Orthopaed. Res.* 11:256-62, 1993); heparin (Tamargo et al., *J. Neurooncol.* 9:131-8, 1990); interleukin-12 (Kuriakose et al., *Head & Neck* 22:57-63, 2000); naproxen (Conforti et al., *J. Pharm. Pharmacol.* 48:468-73, 1996); nerve growth factor (Camerata et al., *Neurosurgery* 30:313-19, 1992); retroviral vector producer cells to transfer a cytotoxic gene product (Beer et al., *Adv. Drug Deliver. Rev.* 27:59-66, 1997); taxol (Park et al., *J. Controlled Rel.* 52:179-189, 1998; and Harper, E et al., *Clin. Cancer Res.,* 5:4242-4248, 1999); tetanus toxoid (Alonso et al., *Vaccine* 12:299-306, 1994); tetracaine hydrochloride (Ramirez et al., *Microencap.* 16:105-15, 1999); tirapazamine (Yuan et al., *Radiation Oncol. Investig.* 7:218-30, 1999); thyrotropin-releasing hormone (Kubek et al., *Brain Res.* 809:189-97, 1998); and vaccines (Chattaraj et al., *J. Controlled Rel.* 58:223-32, 1999). Other therapeutically active substances that can be combined with a biocompatible component include: anesthetics, angiogenesis inhibitors (e.g., Lau D. H. et al., *Cancer Biother. Radiopharm.* 14:31-6, 1999), antibiotics (e.g., Bahk J. Y. et al., *J. Urol.* 163:1560-4, 2000; and Miyamoto H. et al., *Current Eye Research* 16:930-5, 1997), antibodies (e.g., Gomez S. M. et al., *Biotechnol. Prog.* 15:238-44, 1999), anticoagulants (e.g., Tamargo R. J. et al., J. Neurooncol. 9:131-138, 1990), antigens (e.g., Machluf M. et al., J. Pharm. Sci. 89:1550-57, 2000), anti-inflammatory agents (e.g., Reinhard C. S. et al., J. Controlled Release 16:131-40, 1991; and Tamargo R. J. et al., J. Neurosurg. 74; 956-61 1991), antivirals, apoptosis-inhibiting agents (e.g., Macias D. et al., Anat. Embryol. (Berl) 193:533-41, 1996), cytokines (e.g., Edelman E. R. et al., Biomaterials 12:619-26, 1991), cytotoxic agents (e.g., Brem H. et al., J. Neurosurg, 80:283-90, 1994; Brem H. et al. J. Neurosurg. 80:283-90, 1994; Brem H. et al., Lancet 345:1008-12, 1995; Ewend M. G. et al., Cancer Res. 56:5217-23, 1996; Fung L. K. et al., Cancer Res. 58:672-85, 1998; Grossman S. et al., J.

Neurosurg, 76:640-47, 1992; Kong Q. et al., J. Surgical Oncology 69:76-82, 1998; Shikani A. H. et al., Laryngoscope 110:907-17, 2000; Straw R. C. et al., J. Orthop. Res. 12:871-7, 1994; Tamargo R. J. et al., Cancer Research 53:329-33, 1993; Valtonen S. et al., Neurosurgery 41:44-9, 1997; Walter K. A. et al., Cancer Research 54:2207-12, 1994; Yapp D. T. T. et al, IJROBP 39:497-504, 1997; Yapp D. T. T. et al., Anti-Cancer Drugs 9:791-796, 1998; Yapp D. T. T. et al., IJROBP 42:413-20, 1998; and Yoshida M. et al., Biomaterials 10:16-22, 1989), enzymes (e.g., Park T. G. et al., J. Control Release 55:181-91 1998), gene vectors (e.g., Hao T. et al, J. Control Release 69:249-59, 2000; and Maheshwari A. et al., Mol. Ther. 2:121-30, 2000), hormones (e.g., Rosa G. D. et al., J. Control Release 69:283-95, 2000), immunosuppressants (e.g., Sanchez A. et al., Drug Delivery 2:21-8, 1995), mitogens (e.g., Ertl B. et al., J. Drug Target 8:173-84, 2000), neurotransmitters (e.g., During M. J. et al., Ann Neurology 25:351-6, 1989), radioprotectants (e.g., Monig H. et al., Strahlenther Onkol, 166:235-41, 1990), radiosensitizers (e.g., Williams J. A. et al., IJROBP 42:631-39, 1998; and Cardinale R. M. et al., Radiat. Oncol. Invest. 6:63-70, 1998), stimulating and growth factors, transforming agents (e.g., Hong L. et al., Tissue Eng. 6:331-40, 2000), and viral vectors.

Various known methods and seeds relate to the application of heat to a target tissue for the purpose of kitting cancerous cells (see for example Gordon in U.S. Pat. No. 4,569,836 and Delannoy in U.S. Pat. No. 5,284,144). Prior art metallic seeds known as "thermoseeds" have been described by Paulus in U.S. Pat. No. 5,429,583. In contrast to metal thermoseeds that generate heat mainly by eddy current loss, ferromagnetic microspheres generate heat predominantly by hysteresis loss.

Since it is widely known that clinically relevant heating of tissues can be generated by magnetic hysteresis effects, a preferred embodiment includes a magnetically imbued biodegradable carder within the strands/seeds. Widder described an intravascular version of this kind of ferromagnetic microsphere in U.S. Pat. No. 4,247,406. Mitsumori et al. used a dextran-magnetite degradable starch microsphere in their work on inductive hyperthermia in rabbits (Mitsumori et al., *Int J Hyperthermia* 1994; 10:785-93) Minamimura et al., were the first investigator to show significant anti-tumor efficacy in turn bearing rats who were injected with dextran-magnetite microspheres that were then exposed to magnetic forces to generate heat within the tumors (Minamimura et al., *Int. J. Oncol.* 2000; 161153-8). Moroz et al. described successful beating of deep-seated soft tissue in pigs above the critical 42° C. therapeutic threshold following infusions of magnetic iron oxide-doped polymer microspheres (Moroz et al., *J. Surg. Res.* 2002; 105:209-14).

In addition to polymers and starch, other biodegradable substrates can be incorporated into the seeds described herein, as desired by those skilled in the art. Viroonchatapan et al. used thermosensitive dextral-magnetite magnetolipsomes in their in vitro experiments (Viroonchatapan et al, *Pharm. Res.* 1995; 12:1176-83), while Arcos et al. described a new type of biphasic magnetic glass-ceramic mixed with sol-gel glass that has the capability to act as thermoseeds (Arcos et al., *J. Biomed. Mater. Res.* 2003; 65A:71-8).

The claimed brachytherapy seed or strand may also be used for local cancer therapy. In a preferred embodiment, oxygen, hemoglobin, synthetic hemoglobin-like substances, and drugs that enhance tissue oxygen perfusion are included in the biodegradable substrate. Iwashita described a polymer oxygen carrier in U.S. Pat. No. 4,412,989. Bonaventura described a polymeric hemoglobin carrier in U.S. Pat. No. 4,343,715, and Chang described a biodegradable polymer containing hemoglobin in U.S. Pat. No. 5,670,0173. Kakizaki et al. reported on a lipidheme synthetic microspheric oxygen carrier that released oxygen in tissue in vivo (*Artif. Cells. Blood Substit. Immobil. Biotechnol.* 1994; 22:933-8). Bobofchak et al. recently published their work on a recombinant polymeric hemoglobin designated Hb Minotaur (*Am. J. Physiol. Heart. Circ. Physiol.* 2003; 285:H549-61). Substances that can increase oxygen tension in tissue, include but are not limited to oxygen, L-arginine, papaverine, pentoxifyiline, nicotinamide, and nitric oxide and various vasodilators.

Diagnostic compounds can be magnetic (detectable by MRI), radioopaque (detectable by x-ray), fluorescent (detectable by fluorescent techniques) or ultrasound detectable. These materials are commerically available, as are the systems for detection and measurements.

Radiopaque marker 30 can be made of any substance that can be detected by conventional X-ray imaging techniques. See, e.g., *Fundamentals of Diagnostic Radiology*, 2d ed., William E. Brant and Clyde A. Helms (eds.), Lippincott, Williams and Wilkins, 1999; *Physical Principles of Medical Imaging*, 2d ed., Perry Jr. Sprawls, Medical Physic Publishing, 1995; *Elements of Modern X-ray Physics*, Jens Als-Nielsen and Des McMorrow, Wiley & Sons, 2001; *X-ray and Neutron Reflectivity: Principles and Applications*, J. Daillant et al., Springer-Verlag, 1999; *Methods of X-ray and Neutron Scattering in Polymer Science*, Ryoong-Joon J. Roe, Oxford University Press, 2000; and *Principles of Radiographic Imaging: An Art & A Science*, Richard R. Carlton, Delmar Publishers, 2000. Many such substances that can be used as marker 30 are known including, most notably, high atomic number (i.e., "high Z") elements or alloys or mixtures containing such elements. Examples of these include platinum, iridium, rhenium, gold, tantalum, bismuth alloys, indium alloys, solder or other alloys, tungsten and silver. Many currently used radiopaque markers that might be adapted for use in the seeds described herein include platinum/iridium markers from Draximage, Inc. and International Brachytherapy; gold rods from Bebig GmbH; gold/copper alloy markers from North American Scientific; palladium rods from Syncor; tungsten markers from Best industries; silver rods from Nycomed Amersham; silver spheres from International Isotopes Inc. and Urocor; and silver wire from Implant Sciences Corp. Other radiopaque markers include polymers impregnated with various substances (see, e.g., U.S. Pat. Nos. 6,077,880; 6,077,880; and 5,746,998). Radiopaque polymers are described in European Patent Application 894, 503 filed May 8, 1997; European Patent Application 1,016,423 filed Dec. 29, 1999; and published PCT application WO 96/05872 filed Aug. 21, 1995. Those radiopaque polymers that are biodegradable are preferred in applications where it is desired to have the e implant degrade over time in the implantation site.

Examples of radiopaque markers include platinum, iridium rhenium, gold, tantalum, bismuth, indium, tungsten, silver, or a radiopaque polymer. Suitable radioisotopes include $^{125}$I and $^{103}$Pd.

Sometimes combinations of agents may provide enhanced results. For example, in preferred embodiment, a radiosensitizing agent such as 5-FU, etanidazole, tirapazamine, or BUdR, can be used in combination with IUdR. Various combinations of substances are know to be more effective when used in combination than when used alone. See, e.g, Brem et al., *J. Neurosurg.* 80:283-290, 1994; Ewend et al., *Cancer Res.* 56:5217-5223, 1996; Cardinale, *Radiation Oncol. Investig.* 6:63-70, 1998; Yapp et al., *Radiotherapy* and *Oncol.* 53:77-84, 1999; Yapp, IJROBP 39:497-504, 1997; Yuan et al., *Radiation Oncol. Investig.* 7:218-230, 1999; and Menei et al., *Cancer* 86:325-130, 1999.

In addition to the biodegradable radiopaque market in the seeds/strands, microbubbles may also be incorporated to facilitate ultrasonic detection. Micrometer-sized bubbles are known to be extremely potent scatterers of diagnostic frequencies, as reported by Hilgenfeldt et al. in *Ultrasonics* 2000; 38:99-104. Microbubble manufacturing is outlined by Schutt in U.S. Pat. No. 6,280,704 B1 and Schneider in U.S. Pat. No. 6,485,705 B1. The biodegradable microbubble substrate may be disposed within the seed or strand or on any or all of the outer aspect of the invention, II. Formation of Polymeric Seeds Although described in this application with especial reference to the formation of polymeric strands, it is understood that the same or similar technology can be used to make strands of the inorganic materials referenced above.

In one embodiment, polylactic acid strands can be fabricated using methods including solvent evaporation, hot-melt microencapsulation and spray drying. Polyanhydrides made of bis-carboxyphenoxypropane and sebacic acid or poly (fumaric-co-sebacic) can be prepared by hot-melt microencapsulation. Polystyrene strands can be prepared by solvent evaporation. Hydrogel strands can be prepared by dripping a polymer solution, such as alginate, chitosen, alginate/polyethylenimine (PEI) and carboxymethyl cellulose (CMC), from a reservoir though microdroplet forming device into a stirred ionic bath, as disclosed in WO 93/21906.

One or more diagnostic, therapeutic or prophylactic compound can be incorporated into the polymeric strands either before or after formation.

Solvent Evaporation

Methods for forming strands using solvent evaporation techniques are described in E. Mathiowitz et al., *J. Scanning Microscopy,* 4:329 (1990); L. R. Beck et al., *Fertil. Steril.,* 31:545 (1979); and S. Benita et al., *J. Pharm. Sci.,* 73:1721 (1984). The polymer is dissolved in a volatile organic solvent, such as methylene chloride. A substance to be incorporated is added to the solution, and the mixture is suspended in an aqueous solution that contains a surface active agent such as poly(vinyl alcohol). The resulting emulsion is stirred until most of the organic solvent evaporated, leaving solid seeds or strands. Seeds and strands with different sizes (1-1000 µm diameter) and morphologies can be obtained by this method. This method is useful for relatively stable polymers like polyesters and polystyrene. However, labile polymers, such as polyanhydrides, may degrade during the fabrication process due to the presence of water. For these polymers, some of the following methods performed in completely anhydrous organic solvents are more useful.

Hot Melt Microencapsulation

Seeds can be formed from polymers such as polyesters and polyanhydrides using hot melt methods as described in Mathiowitz et al., *Reactive Polymers,* 6:275 (1987). In this method, the use of polymers with molecular weights between 3-75,000 Daltons is preferred. In this method, the polymer first is melted and then mixed with the solid panicles of a substance to be incorporated that have been sieved to less than 50 µm. The mixture is suspended in a non-miscible solvent (like silicon oil), and, with continuous stirring, heated to 5° C. above the melting point of the polymer. Once the emulsion is stabilized, it is cooled until the polymer particles solidify. The resulting seeds are washed by decantation with petroleum ether to give a free-flowing powder. Seeds and strands with diameters between 1 and 1000 µm are obtained with this method.

Solvent Extraction

This technique is primarily designed for polyanhydrides and is described, for example, in WO 93/21906, published Nov. 11, 1993. In this method, the substance to be incorporated is dispersed or dissolved in a solution of the selected polymer in a volatile organic solvent like methylene chloride. This mixture is suspended by stirring in an organic oil, such as silicon oil, to form an emulsion. Seeds that range between 1-300 µm can be obtained by this procedure.

Spray-Drying

Methods for forming seeds using spray drying techniques are well known in the art. In this method, the polymer is dissolved in an organic solvent such as methylene chloride. A known amount of a substance to be incorporated is suspended (insoluble agent) or co-dissolved (soluble agent) in the polymer solution. The solution or the dispersion then is spray-dried. Seeds ranging between 1 and 10 µm are obtained. This method is useful for preparing seeds tot imaging of the intestinal tract. Using the method, in addition to metal compounds, diagnostic imaging agents such as gases can be incorporated into the seeds.

Phase Inversion

Seeds can be formed from polymers using a phase inversion method wherein a polymer is dissolved in a good solvent, fine particles of a substance to be incorporated, such as a drug, are mixed or dissolved in the polymer solution, and the mixture is poured into a strong non-solvent for the polymer, to spontaneously produce, under favorable conditions, polymeric seeds, wherein the polymer is either coated on the particles or the particles are dispersed in the polymer. The method can be used to produce microparticles in a wide range of sizes, including, for example, about 100 nm to about 10 µm. Exemplary polymers which can be used include polyvinylphenol and polylactic acid. Substances which can be incorporated include, for example, imaging agents such as fluorescent dyes, or biologically active molecules such as proteins or nucleic acids.

Protein Microencapsulation

Protein seeds can be formed by phase separation in a non-solvent followed by solvent removal as described in U.S. Pat. No. 5,271,961 to Mathiowitz et al. Proteins which can be used include prolamines such as zein. Additionally, mixtures of proteins or a mixture of proteins and a bioerodable material polymeric material such as a polylactide can be used. In one embodiment, a prolamine solution and a substance to be incorporated are contacted with a second liquid of limited miscibility with the prolamine solvent, and the mixture is agitated to form a dispersion. The prolamine solvent then is removed to produce stable prolamine seeds without crosslinking or heat denaturation. Other prolamines which can be used include gliadin, hordein and kafirin.

Low Temperature Casting of Seeds

Methods for very low temperature casting of controlled release seeds are described in U.S. Pat. No. 5,019,400 to Gombotz et al. In the method, a polymer is dissolved in a solvent together with a dissolved or dispersed substance to be incorporated, and the mixture is atomized into a vessel containing a liquid non-solvent at a temperature below the freezing point of the polymer-substance solution, which freezes the polymer droplets. As the droplets and non-solvent for the polymer are warmed, the solvent in the droplets thaws and is extracted into the non-solvent, resulting in the hardening of the seeds.

Strands can also be made using many of the above-techniques using extrusion technology to elongate the seeds into strands.

Hydrogel Seeds

Seeds made of gel-type polymers, such as alginate, are produced through traditional ionic gelation techniques. The polymer first is dissolved in an aqueous solution, mixed with a substance to be incorporated, and then extruded through a microdroplet forming device, which in some instances employs a flow of nitrogen gas to break off the droplet. A slowly stirred ionic hardening bath is positioned below the extruding device to catch the forming microdroplets. The seeds are left to incubate in the bath for twenty to thirty minutes in order to allow sufficient time for gelation to occur. Particle size is controlled by using various size extruders or varying either the nitrogen gas or polymer solution flow rates.

Chitosan seeds can be prepared by dissolving the polymer in acidic solution and crosslinking it with tripolyphosphate. Carboxymethyl cellulose (CMC) seeds can be pared by dissolving the polymer in acid solution and precipitating the microsphere with lead ions. Alginate/polyethylene imide (PEI) can be prepared in order to reduce the amount of carboxylic groups on the alginate microcapsule. The advantage of these systems is the ability to further modify their surface properties by the use of different chemistries. In the case of negatively charged polymers (e.g. alginate, CMC), positively charged ligands (e.g., polylysine, polyethyleneimine) of different molecular weights can be ionically attached.

Fluidized Bed

Particles, including seeds, can be formed and/or coated using fluidized bed techniques. One process is the Wurster air-suspension coating process for the coating of particles and seeds. The process consists of supporting the particles in a vertical column of heated air while the particles pass an atomizing nozzle that applies the coating material in the form of a spray. Enteric and film coating of seeds or strands by this process typically requites approximately 30 minutes. Suitable coating materials include, but are not limited to, cellulose acetate phthalate, ethylcellulose, hydroxypropyl methylcellylose, polyethylene glycol, and zein.

The Wurster apparatus provides controlled cyclic movement of the suspended particles by a rising stream of warm air, the humidity, temperature, and velocity of the air regulated. Art air-suspended or fluidized bed of particles has a random movement. If seeds or strands move in and out of a coating zone in a random manner, the coating can be applied only at a slow rate. The Wurster apparatus, however, provides better drying and eventually a more uniform coating by imparting a controlled cyclic movement without or with less randomness. A support grid at the bottom of the vertical column typically includes a course screen, e.g., 10 mesh, and a fine screen, e.g., 200 mesh. The fine screen offers considerably more resistance to the air flow than the coarse screen; thus, the greater amount of air flows through the coarse screen. The air flowing through coarse screen lifts the seeds or strands upward in the column. As the velocity of the air stream is reduced due to diffusion of the stream and resistance of the seeds or strands, the upward movement of the seeds or strands ceases. Then the seeds or strands enter the region of a still lower velocity air stream above the fine screen, where they dry and gently settle. As the dried and partially coated seeds or strands approach the grid, they are again introduced into the higher-velocity air stream and the coarse screen, and enter into another cycle.

Below the grid support for the coarse screen, the coating fluid is dispersed by atomization under pressure. A compressed-air inlet is connected to the atomizing the solution or slurry of the coating material. The seeds or strands, which are suspended above the coarse screen, have little contact with each other, so the coating fluid is readily distributed onto the surface of the seeds or strands in the moving bed. As the cyclic movement of the seeds or strands continues, the seeds or strands are presented many times in many different positions to the atomized spray; therefore, a uniform coating is built up on the seeds or strands. Coating is controlled by the weight of the coated seeds or strands, formulation of the coating, temperature, time, and air velocity. Particle sizes can vary from about 50 µm to about 2 mm or greater.

IV. Method of Making Brachytherapy Strand for Implantation

One method of making a brachytherapy strand for implantation into a subject includes the steps of: (a) providing a non-metal biocompatible component and a therapeutically active diagnostic or prophylactic component (herein referred to as "therapeutically active component"), optimally further including an imaging agent or tracer; (b) physically associating the biocompatible component and the therapeutically active component to from a combination product; and (c) forming the combination product into a strand having a size and shape suitable for passing through the bore of a needle having an interior diameter of less than about 2.7 millimeters (10 gauge), less than about 1.4 millimeters (15 gauge), or less than about 0.84 millimeters (18 gauge), or less than about 0.56 millimeters (24 gauge).

Referring to the drawings the are illustrated various different embodiments of the brachytherapy strands. Although there is no lower limit as to how small any dimension of strand can be, in many applications, those that are not able to pass through bores smaller than 0.3 mm are preferred. For example, in many applications where it is desirable for the implanted brachytherapy strands to maintain their orientation in the tissue, the strand should be large enough to stay lodged at the site of implantation in the desired orientation for a relatively long period, larger strands are preferred. In some cases, the selection of materials for use in the strand will affect its size. For instance, in versions of the strand where the biocompatible component is a stainless steel or titanium capsule, the walls of the capsule may need to be greater than a certain minimum size in order to maintain the structural integrity of the strand. In addition, in some applications, the strand should also be large enough to carry a sufficient amount of the therapeutically active component to be therapeutically active (i.e., a therapeutically effective amount or an amount that exerts a desired medically beneficial effect). In order to facilitate the passage of the strand through the bore of a needle while preventing jamming of the brachytherapy implantation needle bore (e.g., caused by clumping of several strands), it is also preferred that the diameter of strand be just slightly less than the diameter of the bore of the needle (e.g., 0.5-5% less).

For use with the needles used in many conventional brachytherapy strand implantation devices, brachytherapy seeds shaped into a cylinder (or rod) having a diameter of between about 0.8 to 3 millimeters and a length of up to 40 millimeters are preferred. Because many conventional brachytherapy strand applicators make use of brachytherapy implantation needles about 17 to 18 gauge in size, cylindrically shaped brachytherapy strands having a diameter of between about 0.8 and 1.1 mm and a length greater than the diameter (e.g., 2-10 mm) are preferred for use with such applicators. In particular, because many conventional brachytherapy strand applicators are designed to accept conventional radioactive brachytherapy strands that have a diameter of about 0.8 millimeters and a length of about 4.5 millimeters, brachytherapy strands of similar size are especially preferred.

Brachytherapy strands are not limited to those being cylindrical in shape, but rather can be any shape suitable for passing through the bore of a needle. For example, in any cases, the cross-sectional area of the strands can be cuboid, spheroid, ovoid, ellipsoid, irregularly shaped, etc. The ends of the strands can be rounded, squared, tapered, conical, convex, concave, scalloped, angular, or otherwise-shaped. The brachytherapy strands can be solid or have one or more cavities or pores (e.g., to increase the surface area of the strand exposed to the target tissue).

Figure 2:
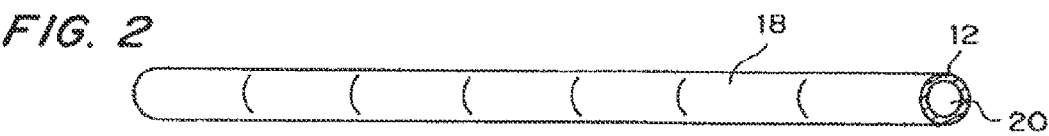
FIG. 2 is a schematic side view of a hollow tube-shaped brachytherapy strand.

FIG. 1 is a schematic side view of a cylindrically shaped brachytherapy strand. FIG. 2 is a schematic side view of a hollow tube-shaped brachytherapy strand.

As one example, as illustrated in FIG. 2, a brachytherapy strand 10 is shaped into a hollow tube 18 having a cylindrical cavity 20. In preferred versions of strand 10, cylindrical cavity 20 is sized to accept and envelop a standard-sized brachytherapy strand (e.g., one having a diameter of about 0.8 mm and a length of about 4.5 mm). For use, the strand 10 can be placed over the standard-sized brachytherapy strand, and introduced into the bore of a needle (sized to accept the enveloped strand) for implantation into a target tissue. The strand 10 shown in FIG. 2 can also be used alone without being placed over a standard-sized brachytherapy strand, e.g., to increase the surface area exposed in the site of implantation. Hollow tube 18 can have any wall thickness or length suitable for wholly or partially enveloping a standard-sized brachytherapy strand and passing through the bore of a needle. Preferably it has a wall thickness between about 0.01 and 0.1 mm and a length of between about 1 to 4.5 mm.

Referring again to FIGS. 1 and 2, biocompatible component 12 can be composed of any material suitable for implantation in a target tissue in an animal subject (e.g., a mammal such as a human patient) that can be associated with therapeutically active component such that all or part of the therapeutically active component will be delivered to the target tissue when the brachytherapy strand 10 is introduced into the implantation site, as discussed above. For ease of use, ease of manufacture, and for therapeutic advantages, it is preferred that the biocompatible component 12 be biodegradable (i.e., made of a substance other than titanium or stainless steel).

A skilled artisan can select the particular composition of the component 12 that is most suited for a given application. For example, where the strand 10 is intended to be used to slowly deliver the therapeutically active component 14 when implanted in a target tissue, a biocompatible and biodegradable material made up of a chemical composition of a polymer known to degrade at a desired rate when placed under conditions similar to those encountered in the implantation site can be selected for use as component 12. Various characteristics of such biodegradable components are described, e.g., in *Biomaterials Engineering and Devices: Human Applications: Fundamentals and Vascular and Carrier Applications*, Donald L. Wise et al. (eds), Humana Press, 2000; *Biomaterials Science: An Introduction to Materials in Medicine*, Buddy D. Ratner et al. (eds). Academic Press, 1997; and *Biomaterials and Bioengineering Handbook*, Donald L. Wise, Marcel Dekker, 2000. For example, by selecting an appropriate material for use as the biocompatible component 12 of the brachytherapy strand 10, the duration of release of the therapeutically active component 14 from strand 10 can be varied from less than about an hour to more than about several months (e.g., 10 min., 30 min., 1 h., 2 h., 3 h., 6 h., 12 h., 1 day, 2 days, 3 days, 1 week, 2 weeks, 1 month, 2 months, 3 months, 4 months, 5 months, 6 months, 1 year, 2 years, or 3 years). Biocompatible component 12 is not limited to being biodegradable. For example, in some cases, component 12 can also be made of a non-biodegradable material such as stainless steel or titanium. In this case, biocompatible component 12 can be coated or otherwise associated with therapeutically active component 14, such that component 14 will be delivered to a target tissue into which strand 10 is implanted. For instance, component 12 might take the form of a porous stainless steel or titanium cylinder having a plurality of pores through its outer surface, such pores being filled with or otherwise in communication with the component 14 such that the component 14 can diffuse from the strand 10 into the environment surrounding the strand 10 (e.g., a target tissue).

These can be tested for suitability in a given application by conventional clinical testing. For example, a test composition can be fashioned into a brachytherapy strand and implanted in a laboratory animal in a selected target tissue. The effects of the implanted compositions on the animal can then be monitored over a period of time. Those that prove to be biocompatible (e.g., not causing an undesired response such as calcification or an allergic response) and have a desired rate of degradation and delivery of a therapeutically active component (if included in the test strand) can thus be identified.

As discussed above, the therapeutically active component 14 is a material that can be (a) implanted in a target tissue of an animal subject (e.g., a mammal such as a human patient) to exert an effect on the animal's physiology, and (b) associated with the biocompatible component 12 in the brachytherapy strand 10. Myriad different substances can be used as the therapeutically active component 14. See, e.g., Physician's Desk Reference, The Merck Index, and USP DI® 2000 published by U.S. Pharmacopeia. For example, the therapeutically active component 14 can include a small molecule drug (e.g., a non-peptide or non-nucleic acid-based molecule with a molecular weight generally less than 5 kDa) such as a chemical with known anti-cancer properties. It can also include a biologic such as a polypeptide (e.g., an antibody or a cytokine) or nucleic acid (e.g., an expression vector). For example, where the strand 10 is intended to be used as a primary treatment for prostate cancer, the therapeutically active substance 14 can include an anti-neoplastic drug such as paclitaxel (taxol), cisplatin, or 5-fluorouracil; or a hormone such as leuprolide. As another example, whole the strand 10 is intended to be used as an adjuvant to radiation treatment for prostate cancer, the therapeutically active substance 14 can include a radio-sensitizing agent such as tirapazamine, BUdR, IUdR, or etanidazole. Because brachytherapy strand 10 allows in situ drug delivery to a tissue, the therapeutically active substance 14 may include a drug that is usually considered too toxic to treat a given condition if given systemically, e.g., tirapazamine or camptothecin.

As indicated in the above description of the brachytherapy strand 10 shown in FIGS. 1 and 2, the biocompatible component 12 is associated with the therapeutically active component 14. As used herein, when referring to the biocompatible component 12 and the therapeutically active component 14, the phrase "associated with" means physically contacting. Thus, in the strand 10, the association of the biocompatible component 12 with the therapeutically active component 14 can take many forms. For example, the biocompatible component 12 and the therapeutically active component 14 can be combined into a mixture as shown in FIGS. 1 and 2. This mixture can have a uniform or non-uniform distribution of components 12 and 14. The brachytherapy strand 10 shown in FIG. 1 is an example of a uniform mixture of components 12 and 14. The brachytherapy strand 10 of this example can be made by simply mixing together the biocompatible component 12 and the therapeutically active component 14 to form a combination product and then forming the product into the desired size and shape, e.g. using a mold.

Although the brachytherapy strands shown in FIGS. 1 and 2 include mixtures of discrete particles dispersed through a matrix consisting of the therapeutically active component 14, in other versions of brachytherapy strand 10, components 12 and 14 are combined in a single particle or in a larger mass without discrete particles (e.g., a pellet the size and shape of brachytherapy strand 10). For example, biocompatible component 12 and therapeutically active component 14 can be dissolved into a liquid and then dried or cured to form strands or a larger pellet made up of a homogeneous distribution of both components 12 and 14. (see, e.g., Ramirez et al., *J. Microencapsulation* 16:105, 1999).

The skilled artisan can select the size according to the desired properties and particular properties of the microsphere constituents. In one variation of this, the strands are also made to include magnetic elements. The strands can then be molded or compressed together into the desired shape and size of brachytherapy strand 10. The larger pellet can likewise be sculpted, extruded, molded or compressed into the desired shape and size of brachytherapy strand 10. Alternatively, the liquid mixture of components 12 and 14 can be poured into a mold defining the shape and size of brachytherapy strand 10, and then cured in the mold. Brachytherapy strands having components 12 and 14 combined in a single particle or in a larger mass (rather than discrete particles of each are advantageous for delivering the therapeutically active component 14 into a target tissue over longer time periods.

In other embodiments of strand 10, components 12 and 14 are not necessarily homogeneously mixed in the strand 10. Rather they can be positioned in different areas of the strand 10. For example, components 12 and 14 can be separately fashioned into discrete sections, strips, coils, tubes, etc. The discrete sections, strips, coils, tubes, etc. of the component 12 can then be combined (e.g., by molding together, adhering, structurally interlocking, etc.) with the discrete sections, strips, coils, tubes, etc. of the component 14 to form the strand 10. In another embodiment, the strand 10 shown in FIG. 2 can be modified by filling the cylindrical cavity 20 with a hydrogel, including a therapeutically active substance, and capping off the ends of the hollow tube 18.

Figure 3A:
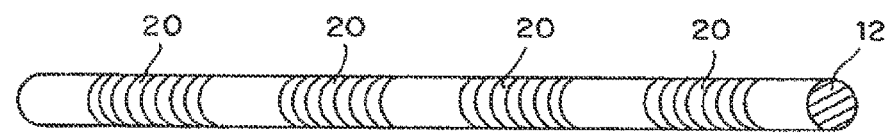
FIGS. 3A-3I are strands with inert spacers, interspersed for cutting (FIG. 3A); with pop-up wings to prevent migration or shifting after implanting (FIG. 3B); with a radiopaque strip running through it (FIG. 3C); with cross-style stabilizers (FIG. 3D); with male and female ends to facilitate joining, e.g., in a ring (FIG. 3E); with indentations for cutting or breaking into smaller strands (FIG. 3F); with a stabilizer, such as bumps (FIG. 3G); a braided strand (FIG. 3H); and strands knotted together (FIG. 3I).
Figure 3B:
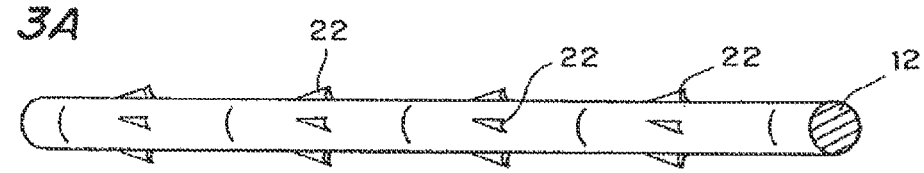
Figure 3C:
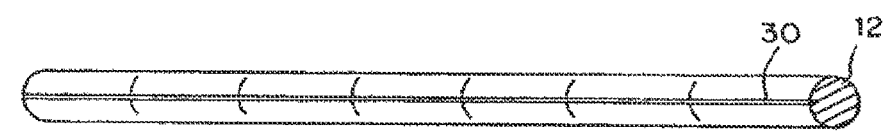
Figure 3D:
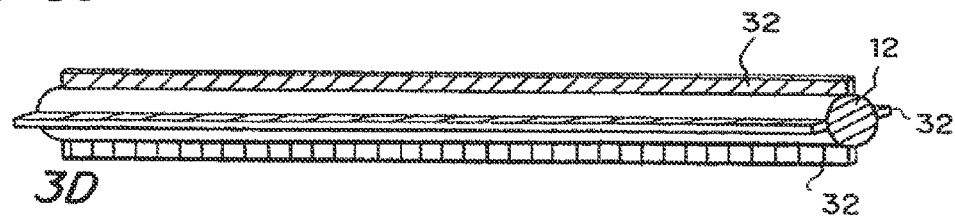
Figure 3E:
Figure 3F:
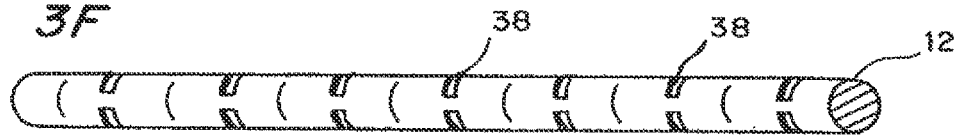
Figure 3G:
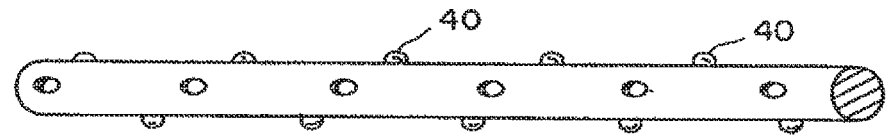
Figure 3H:
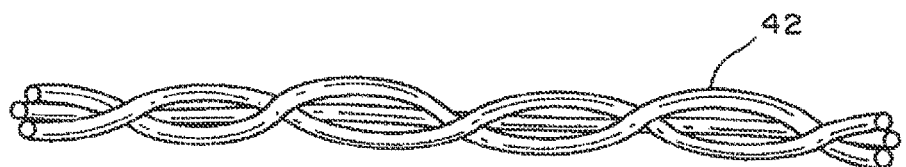
Figure 3I:
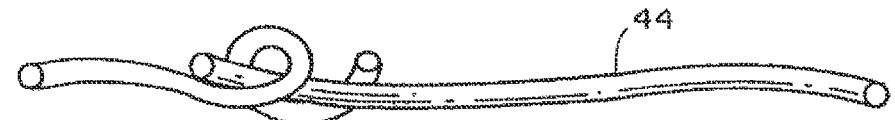
Figure 4A:
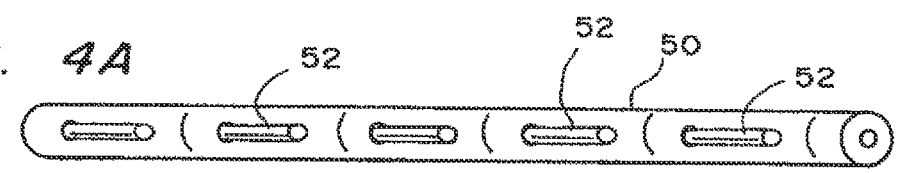
FIGS. 4A and 4B are a strand with radioactive seeds interspersed (perspective view, FIG. 4A; cross-sectional view, FIG. 4B).
Figure 4B:
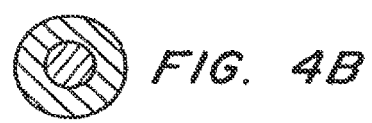

These variations are more clearly understood by reference to the following figures. FIGS. 3A-3I are strands with inert spacers 20, interspersed for cutting (FIG. 3A); with pop-up wings 22 to prevent migration or shifting after implanting (FIG. 3B); with a radiopaque strip 30 running through it (FIG. 3C); with cross-style stabilizers 32 (FIG. 3D); with male 34 and female 36 ends to facilitate joining, e.g., in a ring (FIG. 3E); with indentations 38 for cutting or breaking into smaller strands (FIG. 3F); with a stabilizer, such as bumps 40 (FIG. 3G); as braided strand 42 (FIG. 3H); and strands knotted together 44 (FIG. 3I). FIGS. 4A and 4B are a strand 50 with radioactive seeds 52 interspersed (perspective view, FIG. 4A; cross-sectional view, FIG. 4B).

The foregoing combination products (i.e., at least one biocompatible component mixed with at least one therapeutically active component) can be used in the brachytherapy strands by forming them into a size and shape suitable for passing through the bore of a needle such as one in a conventional brachytherapy strand implantation device. Referring now to FIGS. 3A-I, in others, a brachytherapy strand 10 includes a biocompatible component 12 associated with a therapeutically active component 14, and a radiopaque marker 30 (not shown except in FIG. 3C) attached to the biocompatible component 12 and/or the therapeutically active component 14. Radiopaque marker 30 allows for the position of brachytherapy strand 10 to be determined using standard X-ray imaging techniques (e.g., fluoroscopy) after strand 10 has been implanted in a target tissue. Proper positioning of strand 10 and spacing of a plurality of brachytherapy strands in a given target tissue is important for ensuring that the therapeutically active component 14 is delivered adequately to the site of the disease in the target tissue.

As indicated above, radiopaque marker 30 is attached to strand 10 via the biocompatible component 12 and/or the therapeutically active component 14. The exact manner in which radiopaque marker 30 is attached to strand 10 can is not critical so long as (a) the strand 10 can be passed through the bore of a brachytherapy implantation needle and (b) the attachment allows the position of strand 10 to be readily detected by X-ray imaging. A description of some different examples of how marker 30 can be associated with strand is presented in FIGS. 3A-F. In the embodiment shown in FIG. 3A, the radiopaque marker 30 in the form of a ribbon, filament, strip, thread, or wire is placed in the center and along the length of cylindrical strand 10. In FIG. 3B, the radiopaque marker 30 takes the form of two end caps placed at both ends of cylindrical strand 10. In the embodiment illustrated in FIG. 3C, the radiopaque marker 30 is a coil made of a radiopaque substance running through the length of cylindrical strand 10 as shown. In FIG. 3D, the radiopaque marker 30 takes the form of two beads or pellets placed at two locations along cylindrical strand 10. In the embodiment shown in FIG. 3E, the radiopaque marker 30 takes the form of two bands or rings placed at two locations along the outer surface of cylindrical strand 10. In the strand 10 shown in FIG. 3F, the radiopaque marker 30 takes the form of a mesh formed into cylindrical shape. In the strand 10 shown in FIG. 3G, the radiopaque marker 30 is dispersed throughout the strand in a stippled pattern.

FIGS. 4A and 4B are a strand with radioactive seeds interspersed (perspective view, FIG. 4A; cross-sectional view, FIG. 4B).

A particularly preferred embodiment of a brachytherapy strand having a radiopaque marker is one in which the radiopaque marker is a polymer. In one version of this embodiment, radiopaque polymers are combined with a biocompatible component and a therapeutically active component to form a brachytherapy strand that can be visualized by X-ray imaging. Alternatively, the radiopaque polymer can serve as the biocompatible component. For example, strands made of a radiopaque polymer are co-mingled with strands containing a biocompatible component and strands containing (e.g., encapsulating) a therapeutically active component for strands containing both a biocompatible component and a therapeutically active component). The co-mingled strands are then molded into a radiopaque brachytherapy strand. As another example, the radiopaque polymer, the biocompatible component, and the therapeutically active component can be mixed together into a liquid, and the liquid can be cured to form a solid pellet that can be sculpted, molded, compressed, or otherwise made into the size and shape of a brachytherapy strand. An advantage of preparing a radiopaque brachytherapy strand in this manner is that, after implantation, the entire strand can be visualized by X-ray imaging rather than only a portion of a strand (e.g., as occurs with strands utilizing conventional markers).

Figure 5A:
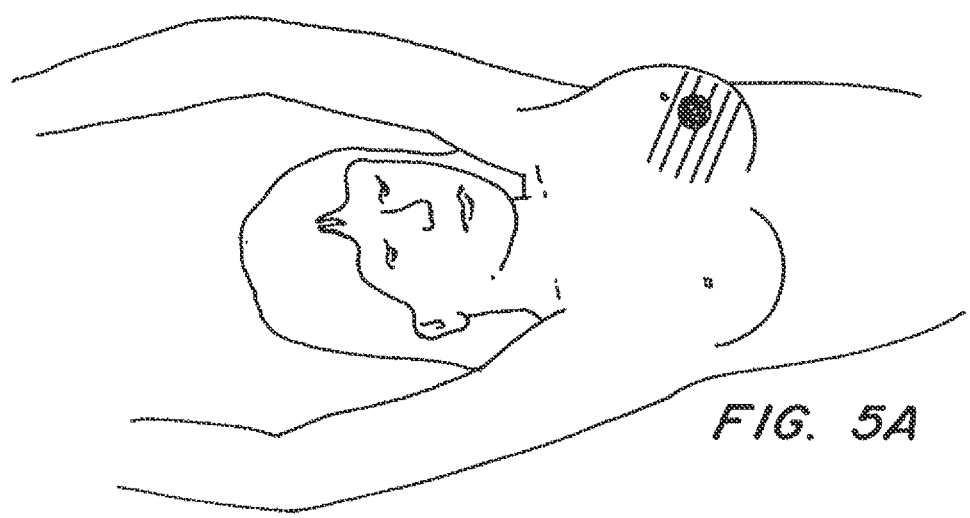
FIGS. 5A-5D are perspective views of strands after introduction into breast adjacent to lumpectomy site (larger circle) below the nipple (smaller circle) (FIG. 5A); strands conforming to shape of breast with patient now upright, lumpectomy site is shown as larger black circle, nipple as smaller circle (FIG. 5B); strand deployed as a coil (FIG. 5C); and strands deployed as rings around lumpectomy site (FIG. 5D).
Figure 5B:
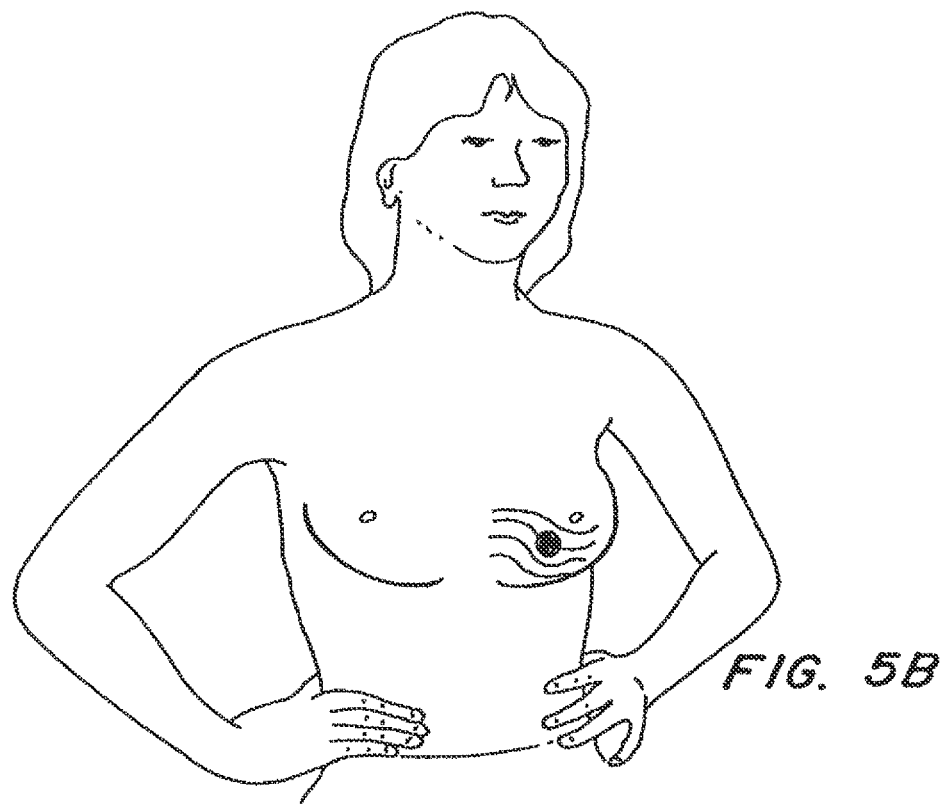
Figure 5C:
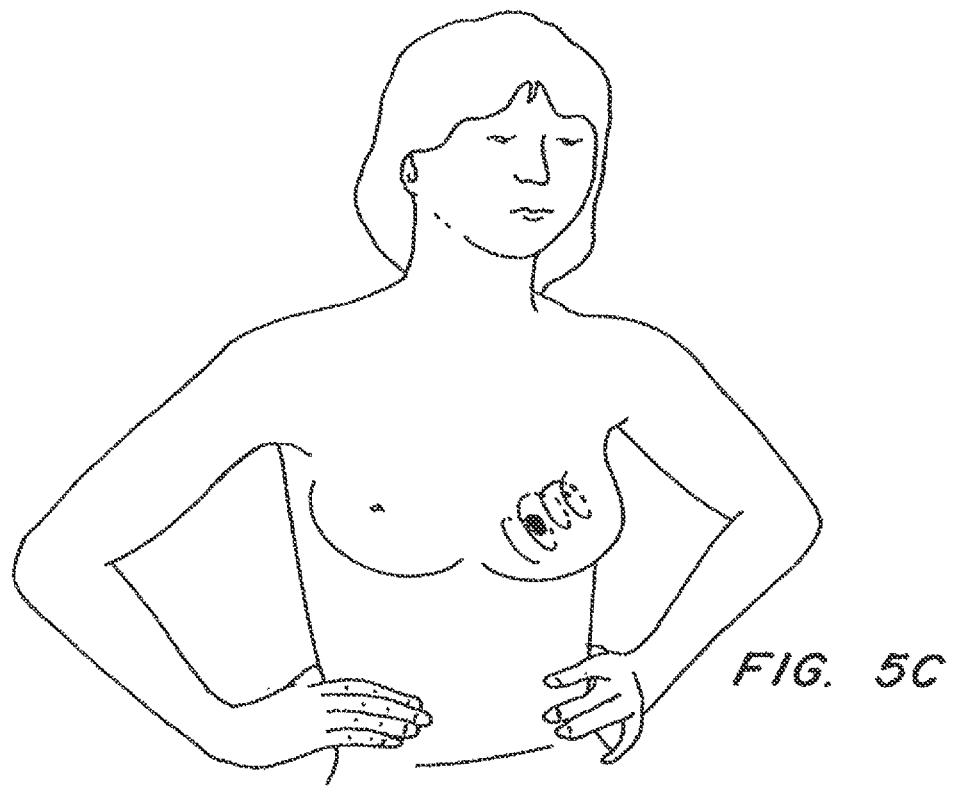
Figure 5D:
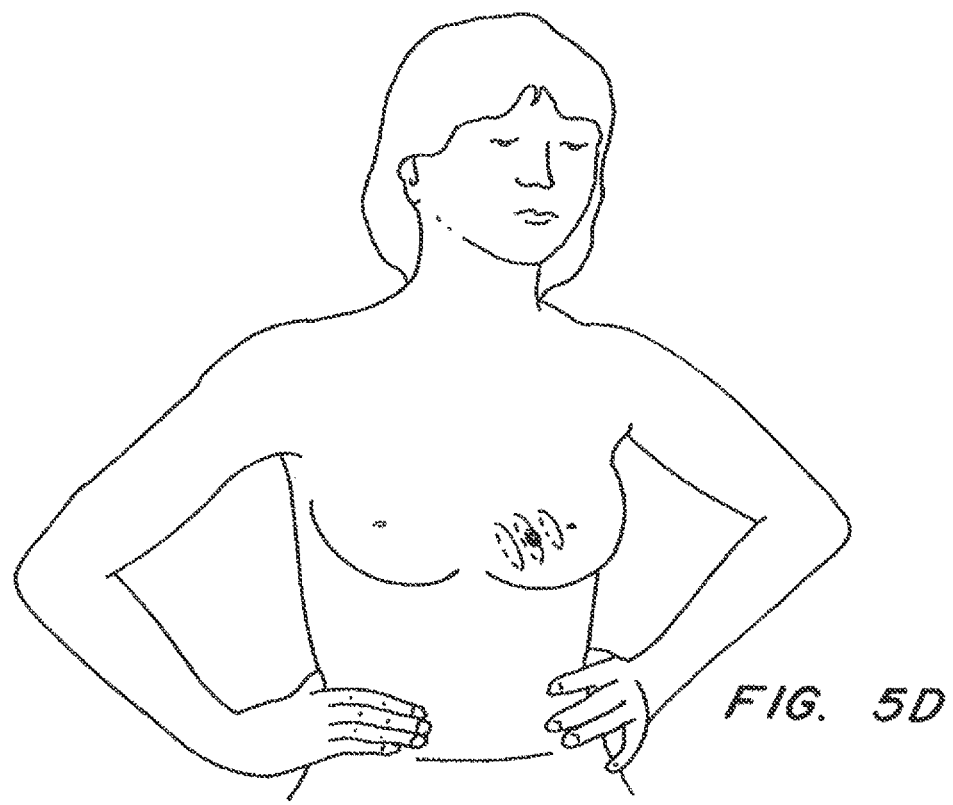

FIGS. 5A-5D are perspective views of strands after introduction into breast adjacent to lumpectomy site (larger circle) below the nipple (smaller circle) (FIG. 5A); strands conforming to shape of breast with patient now upright, lumpectomy site is shown as larger black circle, nipple as smaller circle (FIG. 5B); strand deployed as a coil (FIG. 5C); and strands deployed as rings around lumpectomy site (FIG. 5D).

FIG. 6 is a magnified depiction of microfabricated polyimide hairs. By covering the brachytherapy seed or strand with these polyimide hairs, the problem of seed migration can be effectively overcome. Seed migration involves movement of seeds from their implanted location, usually during the interval immediately following wed placement. Two precipitating causes are felt to be a recoil effect in tissue as it springs back from deformation caused by the seed introducer needle, and suction along the exit path caused by the needle as it is withdrawn after depositing seeds. Several papers in the literature have addressed this issue (see for example, Tapen et al., *IJROBP* 1998; 42:1063-7, Merrick et. al., *IJROBP* 2000; 46:215-20, Poggi et al., *IJROBP* 2003; 56:1248-51).

One method of overcoming this problem is to secure seeds together in a coaxial array within suture strand material such that seeds are kept at a fixed distance from one another. Another approach is to attach each seed to an interlocking peg (see Grimm U.S. Pat. No. 6,450,939B1), again to create a fixed arrangement. However, these systems are fixed by definition, and can present logistical problems when one is working with irregularly shaped targets, or targets that are split by intervening tissue that one wishes to avoid. Furthermore, the strands themselves can migrate, skewing the dosimetry for an entire row of seeds.

Prior art brachytherapy seeds have not satisfactorily addressed the issue of limiting individual seed movement along the needle track. Giem et al have succeeded in producing microfabricated polyimide hairs, and showed that their artificial hairs produce capillary and van der Waals forces which impart particular adhesive properties (Giem et al., *Nature Materials* 2003; 2:461-3). These polyimide hairs have been constructed based on the structure of gecko foot-hairs (setae) which have been shown to have astounding adhesive properties. The polyimide hairs have diameters from 0.2-4 micrometers, heights from 0.15-2 micrometers, and periodicity from 0.4-4.5 micrometers.

The hairs were made as long as possible, and have sufficient flexibility so that individual tips can attach to uneven surfaces all at the same time, and do not break, curl or tangle. Care was taken not to make the hairs too thin, lest they fall down, or too dense, lest they bunch. In order to overcome the problems associated with seed and strand migration, setae technology is used to cover or coat the biodegradable seeds and strands with hairs that impart comparable adhesive potential.

When seeds and strands are implanted into tissues, those tissues are unevenly distributed around the implanted material. The compliant setal structure permits conformance to the shape of a contacting structure, increasing the magnitude of the attractive van der Waals forces as the tiny hairs act together. Similarly, as the seeds and strands are pushed out of their introducing needle, they are dragged over the tissue, which increases setal adhesion. Larger setae create larger sticking forces from larger setal contact areas.

Finally, the tissue is moist since it is living tissue, and setae have improved adhesive properties when they are moist. All of these factors make biodegradable setae (protrusions) an ideal solution to seed/strand migration [see FIG. 6].

FIGS. 7A and 7B illustrate brachytherapy strand geometries such that the brachytherapy strand has one or more conduits running along the length of the strand. These conduits can be pre-filled or fillable, and are useful in the delivery of therapeutic and diagnostic agents to the surrounding implanted tissue. The agents need not be biodegradable themselves, but should be fluid enough to pass through the conduits. Optionally, there can be a pore, series of pores, or network of pores and conduits along the strands through which the agents flow out into the surrounding tissue. In another embodiment, there can be a portal that can be accessed with a needle or other introducer instrument through the skin, or the portal can protrude out of the body via a percutaneous connection to the conduit system. The radioactive material in the strand, if present, can be separated from the conduit system by intervening non-radioactive material. Sundback et al described a similar system in *Biomaterials* 2003; 24:819-30 wherein the conduits were used to contour nerve growth.

The therapeutically active agent 14 in strand 10 including the sealed container 40 can be any of those agents described above. Preferably, however, agent 14 is selected to provide an enhanced effect when used in combination with the radioisotope to treat a particular diseased tissue, as discussed above.

The radioisotope can be any substance that emits electromagnetic radiation (e.g., gamma-rays or X-rays), beta-particles or alpha particles and is suitable for use in brachytherapy strand 10. Examples of such substances include those that decay principally by electron capture followed by X-ray emission such as palladium-103 and iodine-125; isotopes that decay by the emission of beta-particles such as gold-198, gold-199, yttrium-90, and phosphorus-32; isotopes that decay with the emission of both beta-particles and gamma-rays such as indium-192; and isotopes that decay with the emission of alpha-particles such as americium-241. Also useful is gadolinium-157, e.g., for use in boron-neutron capture therapy, and californium-252, rhenium-188, samarium-153, indium-111, ytterbium-169, and holmium-166. For the treatment of prostate cancer, palladium -103 and iodine-125 are preferred as these have been the subject of much clinical investigation for the treatment of the disease. The amount of radioactivity of radioisotope can vary widely. For example, when using palladium-103 or iodine-125, an exemplary amount to treat prostate cancer is respectively about 1.5 mCi and 0.33 mCi per strand, if about 50-150 strands are used at the time of implantation. In other applications the radioactivity per strand can range from about 0.01 mCi to about 100 mCi.

In one embodiment, the radioisotope can be mixed with and then configured into strands, or it can be encapsulated by the biocompatible component to form strands. The radioactive strands cart be molded or otherwise sized and shaped into a brachytherapy strand suitable for implantation via a brachytherapy implantation device. In one version of this embodiment, the biocompatible component is biodegradable such that the radioisotope contained by this component is gradually released from the strand. Alternatively, the biocompatible component and radioisotope can be mixed together and configured as an amorphous pellet having the size and shape of a brachytherapy strand suitable for implantation via a brachytherapy implantation device.

In a preferred embodiment in which the brachytherapy strand contains radionuclide, the strand is coated with a non-radioactive biodegradable coating which degrades at a rate slower than that which allows the radioactivity to leach out, so that radioactivity is not released—i.e., the radioactivity has already fully decayed.

Figure 8A:
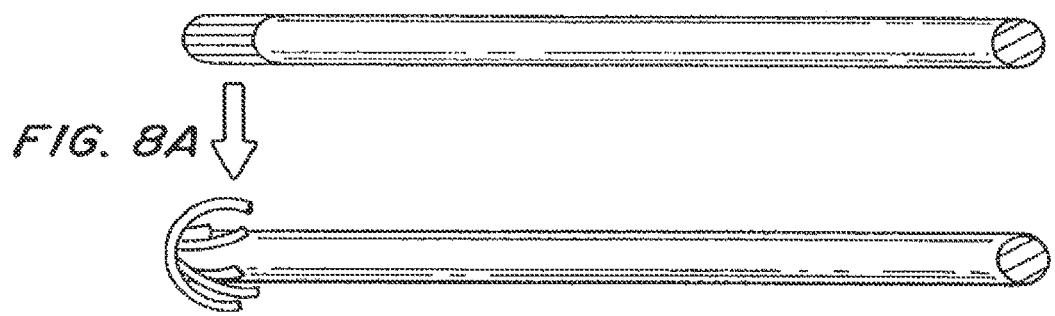
FIGS. 8A and 8B are depictions of a brachytherapy strand equipped with shape memory polymeric anchoring structures at the ends of the strand (FIG. 8A) and interspersed along the length of the strand (FIG. 8B), before and after deployment.
Figure 8B:
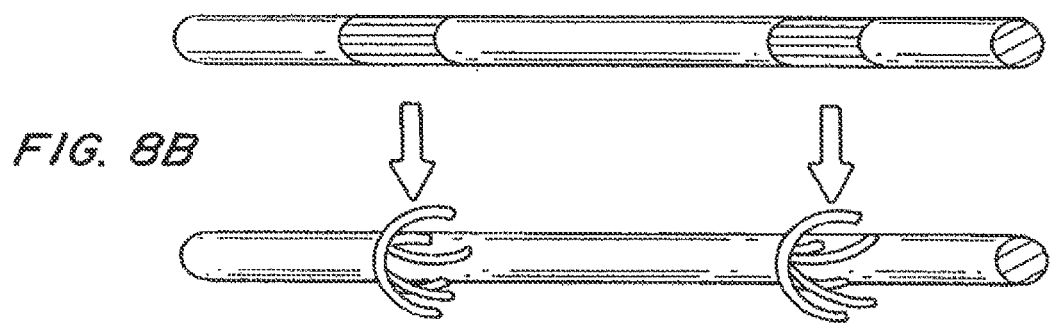
Figure 9:
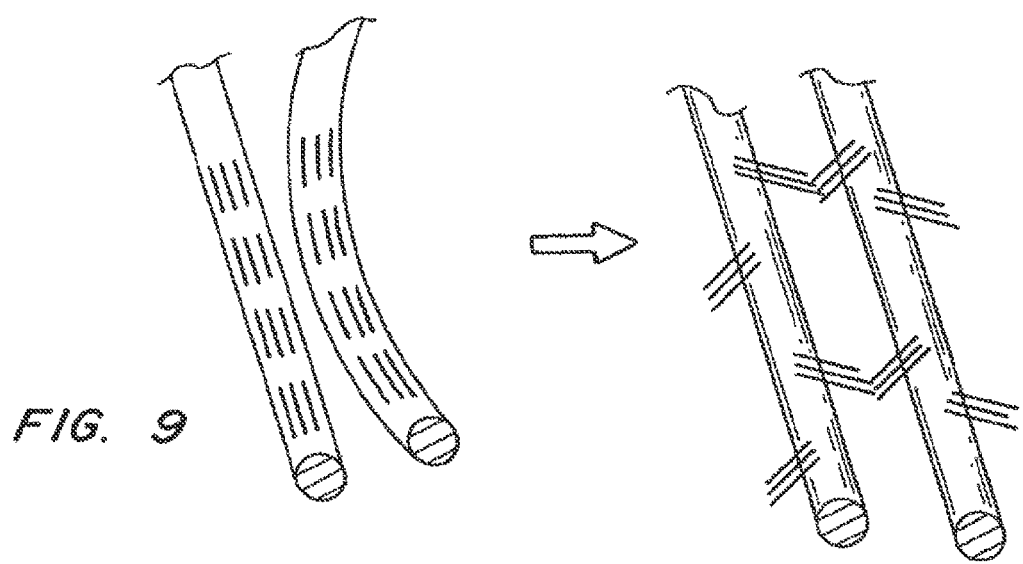
FIG. 9 is a depiction of a brachytherapy strand equipped with shape memory polymeric anchors positioned to brace or center the strands within irregularly shaped tissues.

FIGS. 8A, 8B and 9 depict the addition of polymeric anchoring structures to brachytherapy strands. Biodegradable seeds may also be equipped with as similar system, but on a smaller scale. As noted above, migration can be problematic. Built-in ridges, bumps, and related structures can ameliorate this problem to some extent, but will not completely eliminate it.

Biodegradable shape memory polymeric (Lendlein et al., Science 2002; 296:1673-6) structures which deploy to their pre-trained shape after implantation in order to maintain the seeds in the desired location may also be used. Such structures can ideally include grapple-shaped anchors at the ends of a brachytherapy strand [see FIG. 8A]. These hooks deploy following introduction of the strand into the target tissue. Similar structures can be interspersed the length of the strand, oriented such that the strand becomes locked in position [see FIG. 8B]. The same concept can be used to brace or center the strands within a target tissue in instances where that tissue contains a cavity, defect or other irregular space that might otherwise kink, bend, or offset the strand [see FIG. 9].

These may be bristle-like, ring-shaped, or alternative shapes depending upon the choice made by those skilled in the art. Similarly, they can space apart adjacent strands, thereby avoiding clumping or bunching. Optionally, these structures may or may not contain the therapeutic or diagnostic agents. The shape memory structures are activated by heat from the implanted tissue, or are preheated prior to implantation to trigger their deployment.

As with the shape memory polymer above, electroactive polymers (EAPs) or polymer hybrids may be used for stabilization, spacing, or related purposes. Hybrid substrates can include biodegradable polymer/semiconductor composites. These components expand, contract, bend, or otherwise change shape or size displacement upon exposure to an applied voltage. These types of changes can be induced with very low voltage input which can be achieved without harming the host tissue. Pelrine described this style device in U.S. Pat. No. 6,545,384 B1, as did Kombluh in U.S. Pat. No. 6,586,859B2.

Electronic EAPs can include ferroelectric polymers, dielectric polymers, electrorestrictive graft elastomers, electro-viscoelastic elastomers, liquid crystal elastomer materials, or other related polymers or organic substances. Ionic EAPs can include ionic polymer gels, ionomeric polymer-metal composites, conductive polymers, carbon nanotubes, or other related polymers or organic substances (see for example Bar-Cohen et al., ed., *Electroactive Polymers and Rapid Prototyping: Materials Research Society Symposium Proceedings*, Materials Research, 2002; *Applications of Electroactive Polymers*, (Stienen, ed.), Kluwer Academic Publishers, 1993; Zhang et al., *Nature* 2002; 419:284-7). Scheibel et al. described the use of biomolecular templates as conducting nanowires in *PNAS* 2003; 100:4527-32. In this instance, amyloid formed by prions was the biomolecular substance used to create the nanowires. Various physicochemical factors, such as light, temperature, and pH can be applied to the "small polymers" or other substrates to achieve similar configuration modification.

Spacers can be made of a biocompatible material that can be used to join two brachytherapy seeds. See, e.g., U.S. Pat. No. 6,010,446. The biocompatible material can be either biodegradable or non-biodegradable. For example, spacers can be made of catgut or a like materials. Spacers designed for use with conventional radioactive brachytherapy seeds can be used in chain. For example, Ethicon, Inc. (Cincinnati, Ohio) manufactures the PG 940 non-sterile autoclavable spacer for Indigo (Cincinnati, Ohio) that is sold in conjunction with an Express Seed Cartridge. In addition, Medical Device Technologies, Inc. (Gainesville, Fla.) distributes a pre-sterilized 5.5 mm long absorbable pre-cut spacer that is made of collagen (Look®, model number 1514b). Materials for use as the spacer are also manufactured by Surgical Specialties Corp. (Reading Pa.). Where the spacer is made of a relatively flexible material, the chain can be relatively flaccid.

Where the brachytherapy strand or linker is formed of an elastic polymer such as elastin-like peptides, polyhydroxy-alkanoates (PHAs) or poly(glycol-sebacate), or some protein, the strand or chain is becomes high deformable. Such deformability is particularly advantageous when implanting tissues or organs whose shape may become distorted by normal body motion, such as the breasts or viscera. Where the chain is endowed with the flexibility of an elastic polymer or similar substance, the chain may be considered to be variably flexible rather than rigid or flaccid. The precise degree of flexibility will depend upon the composition of the carrier matrix. Those skilled in the art will be accustomed to selecting the ration of component substances in the carder matrix such that the desired degree or flexibility is achieved. This flexibility, rather than being simply linear or curved, can be in any direction. In some embodiments, the chain may be spiral-shaped or otherwise twisted, springy, or bent to conform to the desired shape. In other embodiments, the chain can form a lattice or mesh whereby one or more chains can be interconnected through baking mechanisms, knots ties, welds, fusions, or other methods known to those skilled in the art. In yet another embodiment, the chain may be introduced into the target tissue in one shape, only to be purposefully or intentionally modified or altered to another advantageous shape thereafter.

Spacers can be connected to seed by any means known. For example, spacer can be connected to seed by direct attachment such as by gluing, crimping, or melting. Spacers can be attached to any portion of the seed. For rod or cylinder-shaped seeds, to facilitate implantation, it is generally preferred that spacers are attached to the ends of the seeds so that the ends are adjacent to one another when the chain is inserted into the barrel of a brachytherapy implantation needle. In one preferred embodiment, the spacer and seed are indistinguishably linked such that no seams, welds, or joints are visible. In another embodiment, the spacer may be of a different color, texture, diameter, hardness, or shape for easy identification and demarcation. This can include a translucent coloration. In still another embodiment, the spacer may be indented or otherwise marked somewhere along its length as an indication of where the seed/spacer chain can be safely cut, spliced, broken, or otherwise separated without exposing active therapeutic substances such as radionuclides that are contained within the seed.

In another embodiment, spacers may be emitted in favor of a continuous array of seeds that may form a chain or strand. This is especially advantageous when implanting an organ such as the breast, where discrete seeds are not necessarily required to achieve the desired dispersement of radioactivity and/or other therapeutic substances. The continuous seed array without interruption by spacer is especially preferred when the implanted strands contain an elastic polymer or other flexible carder for use in a mobile organ or tissue. In yet another embodiment, spacers may be located at varying distances from one another, separated by different lengths of continuous seed arrays, depending upon the clinical circumstances. Depending upon the discretion of the clinician, more than one continuous seed and/or spacer array may be implanted along a given row to achieve the desired effect in tissue.

Where spacers are used, spacer and seed, however, need not be physically attached to each other. Rather they can also be associated with each other by placing each with within the lumen of a tube. The tube can be used to load a brachytherapy seed implantation device with a plurality of spacers and seeds in any sequence. For example, the brachytherapy seed implantation device can loaded with one (or 2, 3, 4, 5, or more) spacer being interposed between every two seeds. Similarly, the brachytherapy seed implantation device can be loaded with one (or 2, 3, 4, 5, or more) seed being interposed between every two spacers.

VI. Methods of Implantation

The brachytherapy strands are implanted into a target tissue within a subject (e.g., a human patient or a non-human animal) by adapting known methods for implanting conventional radioactive brachytherapy seeds into a tissue. For example, the brachytherapy strands can be implanted using one or more implantation needles; Henschke, Scott, or Mick applicators; or a Royal Marsden gold grain gun (H. J. Hodt et al., *British J. Radiology*, pp. 419-421, 1952). A number of suitable implantation devices are described in, e.g., U.S. Pat. Nos. 2,269,963; 4,402,308; 5,860,909; and 6,007,474.

In many applications to treat a given target tissue with a therapeutic agent, it is desirable (or even ideal) to fully saturate the target tissue with the therapeutic agent, while avoiding under- or over-dosing the target tissue. This can be achieved by implanting the brachytherapy strands into a target tissue using a brachytherapy implantation device so that a precise number of strands can be implanted in precise locations within the target tissue. By previously calculating the rate of diffusion of the therapeutically active substance under experimental conditions (e.g., using tissue from animal models), an appropriate dosage can be delivered to the target tissue. Because use of brachytherapy implantation devices allows the brachytherapy strands to be implanted in any number of different desired locations and/or patterns in a tissue, this method advantageous over methods where a drug or drug impregnated matrix is simply placed on the surface of a tissue or manually inserted into a surgically dissected tissue.

In one preferred method of use, the strands are introduced into the target organ through a puncture site with a brachytherapy needle, obviating the need for an incision, suturing of a catheter, tracheostomy, or prolonged insertion of an often uncomfortable or painful metallic or plastic foreign body into the patient. In the case of the base of tongue, the hairpin needles are withdrawn following loading of the strands, thereby limiting the degree of swelling that occurs and possibly sparing the patient the need for a tracheostomy. In the case of a lumpectomy for removal of a breast cancer, the strands can be placed in the same fashion as temporary iridium-192 or iodine-125 metallic seed strands, but without the sutures and buttons anchoring the catheters or needles and strands to the skin retrieval later.

I claim:

1. A flexible non-radioactive strand for implantation into a subject, comprising:
    a marker component configured to allow for the determination of the position of the strand within a target tissue, the marker component having a length extending along a centerline of the marker component between a first end and a second end and having a substantially continuous wall bounding a hollow interior; a biocompatible component; and
    a therapeutic, prophylactic, and/or diagnostic agent, wherein the marker, biocompatible component and agent are disposed within the hollow interior;
    wherein the length of the marker component is greater than the diameter of the hollow interior, and
    wherein the substantially continuous wall includes at least one opening adapted to allow the agent to pass out of the hollow interior wherein the strand do not contain a radioisotope.

2. The flexible strand according to claim 1 wherein the marker component has a maximum length of between one and 50 cm.

3. The flexible strand according to claim 2, wherein the marker component has a maximum length of 40 mm and a diameter between about 0.8 and 3 mm.

4. The flexible strand according to claim 1 wherein at least one of the marker component and the agent is imageable.

5. The flexible strand according to claim 4 wherein the marker component is imageable.

6. The flexible strand according to claim 1 wherein the substantially continuous wall comprises one or more biodegradable structures effective to maintain orientation in tissue, one or more compliant setal or hair structures which impart adhesive properties upon implantation into a target tissue, or combinations thereof.

7. The flexible strand of claim 6, wherein the structures to maintain location or orientation comprise a smart polymer, a shape memory polymer, or other substrate to achieve configuration modification.

8. The flexible strand according to claim 6 wherein the structures include an anchor.

9. The flexible strand according to claim 1, wherein the hollow interior comprises a biocompatible component, and wherein the marker component and the agent are dispersed in the biocompatible component.

10. The flexible strand according to claim 1 wherein the agent is intermixed with the marker component.

11. The flexible strand according to claim 10 wherein the marker component is biodegradable.

12. The flexible strand according to claim 9 wherein the biocompatible component is configured to degrade over time at the implantation site and release the agent by controlling the rate of degradation and/or release rate at the implantation site.

13. The flexible strand according to claim 1 wherein the marker component comprises a high Z material.

14. The flexible strand according to claim 1 wherein the at least one opening comprises the first and/or second ends of the substantially continuous wall.

15. The flexible strand according to claim 1 wherein the agent is selected from the group consisting of an anti-inflammatory, anti-coagulant, cytostatic, antibiotic, anti-neoplastic, vasodilator, anti-viral, immunosuppressive, growth factor, pro-agent, hormone, radiotherapeutic, radiopaque, peptide, protein, enzyme, or combinations thereof.

16. The flexible strand according to claim 1 wherein the strand is configured to release the agent over three years.

17. The flexible strand according to claim 1 wherein the strand is configured to release the agent in less than three years.

18. The flexible strand of claim 1, wherein the agent exerts an effect on the subject's physiology following release.

19. The flexible strand of claim 1, wherein the strand is configured to be implanted into a target tissue in the subject using one or more implantation needles.

20. A flexible, non-radioactive strand comprising a marker component and a therapeutic, prophylactic, and/or diagnostic agent, the agent, marker, or both, being imageable,
   the marker component having a length extending along a centerline of the marker component between a first end and a second end and having a substantially continuous wall along the length, the substantially continuous wall bounding a hollow interior and at least partially enveloping the agent within the hollow interior, and
   wherein the length of the marker component is greater than an average diameter of the hollow interior and the substantially continuous wall includes at least one opening adapted to allow the agent to pass out of the hollow interior wherein the strand do not contain a radioisotope.

21. The flexible strand according to claim 20, wherein the marker component comprises an imageable substrate and the agent is dispersed in the substrate.

22. The flexible strand according to claim 20, further comprising a substrate comprising a biodegradable material, the marker and the agent.

23. The flexible strand according to claim 20 wherein the strand is configured to release the agent over three years or less.

24. The flexible strand of claim 20, wherein the agent exerts an effect on the subject's physiology following release.

25. The flexible strand of claim 20, wherein the strand is configured to be implanted into a target tissue in the subject using one or more implantation needles.

* * * * *

(12) INTER PARTES REVIEW CERTIFICATE (2047th)
United States Patent (10) Number: US 9,636,401 K1
Kaplan (45) Certificate Issued: Apr. 19, 2021

(54) FLEXIBLE AND/OR ELASTIC BRACHYTHERAPY SEED OR STRAND

(71) Applicant: Edward J. Kaplan

(72) Inventor: Edward J. Kaplan

(73) Assignee: MICROSPHERIX LLC

Trial Number:

IPR2018-00402 filed Dec. 29, 2017

Inter Partes Review Certificate for:

Patent No.: 9,636,401
Issued: May 2, 2017
Appl. No.: 14/473,159
Filed: Aug. 29, 2014

The results of IPR2018-00402 are reflected in this inter partes review certificate under 35 U.S.C. 318(b).

INTER PARTES REVIEW CERTIFICATE
U.S. Patent 9,636,401 K1
Trial No. IPR2018-00402
Certificate Issued Apr. 19, 2021

AS A RESULT OF THE INTER PARTES REVIEW PROCEEDING, IT HAS BEEN DETERMINED THAT:

Claims 1-5 and 9-25 are found patentable.

* * * * *